(12) United States Patent
Girouard et al.

(10) Patent No.: US 7,764,995 B2
(45) Date of Patent: Jul. 27, 2010

(54) METHOD AND APPARATUS TO MODULATE CELLULAR REGENERATION POST MYOCARDIAL INFARCT

(75) Inventors: Steven D. Girouard, Woodbury, MN (US); Jeffrey Ross, Roseville, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 330 days.

(21) Appl. No.: 10/862,716

(22) Filed: Jun. 7, 2004

(65) Prior Publication Data

US 2005/0288721 A1 Dec. 29, 2005

(51) Int. Cl.
*A61N 1/36* (2006.01)
(52) U.S. Cl. .......................... 607/3; 607/120
(58) Field of Classification Search ...................... 607/2, 607/3, 32, 60, 120; 604/890.1, 891.1
See application file for complete search history.

(56) References Cited

U.S. PATENT DOCUMENTS

| | | | |
|---|---|---|---|
| 3,692,027 A | 9/1972 | Ellinwood, Jr. |
| 4,003,379 A | 1/1977 | Ellinwood, Jr. |
| 4,146,029 A | 3/1979 | Ellinwood, Jr. |
| 4,281,664 A | 8/1981 | Duggan |
| 4,299,220 A | 11/1981 | Dorman |
| 4,544,371 A | 10/1985 | Dormandy, Jr. et al. |
| 4,556,063 A | 12/1985 | Thompson et al. |
| 4,677,989 A | 7/1987 | Robblee |
| 4,686,987 A | 8/1987 | Salo et al. |
| 4,871,351 A | 10/1989 | Feingold |
| 4,897,987 A | 2/1990 | Spalla |
| 4,902,508 A | 2/1990 | Badylak et al. |
| 4,924,875 A | 5/1990 | Chamoun |
| 4,938,231 A | 7/1990 | Milijasevic et al. |
| 4,944,299 A | 7/1990 | Silvian |
| 4,987,897 A | 1/1991 | Funke |
| 5,014,698 A | 5/1991 | Cohen |

(Continued)

FOREIGN PATENT DOCUMENTS

EP 0054138 6/1982

(Continued)

OTHER PUBLICATIONS

Badylak, Stephen F., et al., "Marrow-Derived Cells Populate Scaffolds Composed of Xenogeneic Extracellular Matrix", *Experimental Hematology*, 29(11), (Nov. 2001), 1310-8.

(Continued)

*Primary Examiner*—Carl H Layno
*Assistant Examiner*—Yun Haeng Lee
(74) *Attorney, Agent, or Firm*—Schwegman, Lundberg Woessner, P.A.

(57) ABSTRACT

A system delivers cardiac pacing therapy and chemical and/or biological therapy to modulate myocardial tissue growth in a heart after myocardial infarction (MI). The system includes an agent delivery device to release one or more agents to an MI region to modulate myocardial tissue growth in that region, and a cardiac rhythm management (CRM) device to deliver pacing pulses to enhance the effects of the one or more agents by altering myocardial wall stress and cardiac workload. In one embodiment, the system is an implantable system including an implantable agent delivery device and an implantable CRM device.

41 Claims, 6 Drawing Sheets

U.S. PATENT DOCUMENTS

| | | |
|---|---|---|
| 5,025,786 A | 6/1991 | Siegel |
| 5,031,621 A | 7/1991 | Grandjean et al. |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,087,243 A | 2/1992 | Avitall |
| 5,103,821 A | 4/1992 | King |
| 5,109,842 A | 5/1992 | Adinolfi |
| 5,127,404 A | 7/1992 | Wyborny et al. |
| 5,130,141 A | 7/1992 | Law et al. |
| 5,190,035 A | 3/1993 | Salo et al. |
| 5,220,917 A | 6/1993 | Cammilli et al. |
| 5,251,621 A | 10/1993 | Collins |
| 5,259,380 A | 11/1993 | Mendes et al. |
| 5,269,301 A | 12/1993 | Cohen |
| 5,275,826 A | 1/1994 | Badylak et al. |
| 5,284,136 A | 2/1994 | Hauck et al. |
| 5,305,745 A | 4/1994 | Zacouto |
| 5,312,453 A | 5/1994 | Shelton et al. |
| 5,314,430 A | 5/1994 | Bardy |
| 5,336,252 A | 8/1994 | Cohen |
| 5,342,408 A | 8/1994 | deCoriolis et al. |
| 5,347,241 A | 9/1994 | Panaretos et al. |
| 5,352,463 A | 10/1994 | Badylak et al. |
| 5,353,800 A | 10/1994 | Pohndorf et al. |
| 5,354,264 A | 10/1994 | Bae et al. |
| 5,368,028 A | 11/1994 | Palti |
| 5,387,419 A | 2/1995 | Levy et al. |
| 5,404,877 A | 4/1995 | Nolan et al. |
| 5,416,695 A | 5/1995 | Stutman et al. |
| 5,423,883 A | 6/1995 | Helland |
| 5,435,999 A | 7/1995 | Austin |
| 5,456,692 A | 10/1995 | Smith, Jr. et al. |
| 5,460,605 A | 10/1995 | Tuttle et al. |
| 5,486,359 A | 1/1996 | Caplan et al. |
| 5,496,360 A | 3/1996 | Hoffmann et al. |
| 5,499,971 A | 3/1996 | Shapland et al. |
| 5,507,724 A | 4/1996 | Hofmann et al. |
| 5,538,722 A | 7/1996 | Blau et al. |
| 5,543,318 A | 8/1996 | Smith et al. |
| 5,551,953 A | 9/1996 | Lattin et al. |
| 5,554,389 A | 9/1996 | Badylak et al. |
| 5,556,421 A | 9/1996 | Prutchi et al. |
| 5,558,632 A | 9/1996 | Lloyd et al. |
| 5,562,713 A | 10/1996 | Silvian |
| 5,571,151 A | 11/1996 | Gregory |
| 5,579,876 A | 12/1996 | Adrian et al. |
| 5,580,779 A | 12/1996 | Smith et al. |
| 5,586,556 A | 12/1996 | Spivey et al. |
| 5,602,301 A | 2/1997 | Field |
| 5,603,331 A | 2/1997 | Heemels et al. |
| 5,607,418 A | 3/1997 | Arzbaecher |
| 5,609,629 A | 3/1997 | Fearnot et al. |
| 5,610,172 A | 3/1997 | Weidmann et al. |
| 5,634,899 A | 6/1997 | Shapland et al. |
| 5,662,689 A | 9/1997 | Elsberry et al. |
| 5,681,735 A | 10/1997 | Emerson et al. |
| 5,690,682 A | 11/1997 | Buscemi et al. |
| 5,693,075 A | 12/1997 | Plicchi et al. |
| 5,703,125 A | 12/1997 | Bovy et al. |
| 5,704,908 A | 1/1998 | Hofmann et al. |
| 5,720,770 A | 2/1998 | Nappholz et al. |
| 5,730,125 A | 3/1998 | Prutchi et al. |
| 5,733,313 A | 3/1998 | Barreras, Sr. et al. |
| 5,733,727 A | 3/1998 | Field |
| 5,741,319 A | 4/1998 | Woloszko et al. |
| 5,800,498 A | 9/1998 | Obino et al. |
| 5,807,306 A | 9/1998 | Shapland et al. |
| 5,817,131 A | 10/1998 | Elsberry et al. |
| 5,824,049 A | 10/1998 | Ragheb et al. |
| 5,833,603 A | 11/1998 | Kovacs et al. |
| 5,833,978 A | 11/1998 | Tremblay |
| 5,834,029 A | 11/1998 | Bellamkonda et al. |
| 5,836,935 A | 11/1998 | Ashton et al. |
| 5,849,033 A | 12/1998 | Mehmanesh et al. |
| 5,855,610 A | 1/1999 | Vacanti et al. |
| 5,865,787 A | 2/1999 | Shapland et al. |
| 5,873,904 A | 2/1999 | Ragheb et al. |
| 5,885,797 A | 3/1999 | Chen et al. |
| 5,893,881 A | 4/1999 | Elsberry et al. |
| 5,899,928 A | 5/1999 | Sholder et al. |
| 5,914,242 A | 6/1999 | Honkanen et al. |
| 5,925,066 A | 7/1999 | Kroll et al. |
| 5,928,943 A | 7/1999 | Franz et al. |
| 5,944,710 A | 8/1999 | Dev et al. |
| 5,945,577 A | 8/1999 | Stice et al. |
| 5,949,659 A | 9/1999 | Lesche |
| 5,967,986 A | 10/1999 | Cimochowski et al. |
| 5,968,006 A | 10/1999 | Hofmann |
| 5,991,668 A | 11/1999 | Leinders et al. |
| 6,005,009 A | 12/1999 | Murad et al. |
| 6,016,447 A | 1/2000 | Juran et al. |
| 6,016,448 A | 1/2000 | Busacker et al. |
| 6,048,722 A | 4/2000 | Farb et al. |
| 6,050,980 A | 4/2000 | Wilson |
| 6,059,726 A | 5/2000 | Lee et al. |
| 6,066,094 A * | 5/2000 | Ben-Haim ............... 600/437 |
| 6,078,834 A | 6/2000 | Lurie et al. |
| 6,083,930 A | 7/2000 | Roufa et al. |
| 6,090,622 A | 7/2000 | Gearhart et al. |
| 6,096,070 A | 8/2000 | Ragheb et al. |
| 6,096,347 A | 8/2000 | Geddes et al. |
| 6,099,832 A | 8/2000 | Mickle et al. |
| 6,100,242 A | 8/2000 | Hammond |
| 6,110,459 A | 8/2000 | Mickle et al. |
| 6,112,116 A * | 8/2000 | Fischell et al. ............ 600/517 |
| 6,114,164 A | 9/2000 | Dennis et al. |
| 6,115,636 A | 9/2000 | Ryan |
| 6,117,296 A | 9/2000 | Thomson |
| 6,119,554 A | 9/2000 | Plankenhorn |
| 6,128,526 A | 10/2000 | Stadler et al. |
| 6,132,419 A | 10/2000 | Hofmann |
| 6,135,976 A | 10/2000 | Tachibana et al. |
| 6,140,740 A | 10/2000 | Porat et al. |
| 6,151,525 A * | 11/2000 | Soykan et al. ............... 607/50 |
| 6,152,955 A | 11/2000 | KenKnight et al. |
| 6,154,675 A | 11/2000 | Juran et al. |
| 6,155,267 A | 12/2000 | Nelson |
| 6,156,572 A | 12/2000 | Bellamkonda et al. |
| 6,165,164 A | 12/2000 | Hill et al. |
| 6,168,801 B1 | 1/2001 | Heil, Jr. et al. |
| 6,174,871 B1 | 1/2001 | Hammond et al. |
| 6,184,030 B1 | 2/2001 | Katoot et al. |
| 6,185,461 B1 | 2/2001 | Er |
| 6,198,394 B1 | 3/2001 | Jacobsen et al. |
| 6,200,265 B1 | 3/2001 | Walsh et al. |
| 6,203,495 B1 | 3/2001 | Bardy |
| 6,206,914 B1 | 3/2001 | Soykan et al. |
| 6,207,451 B1 | 3/2001 | Dennis et al. |
| 6,213,942 B1 | 4/2001 | Flach et al. |
| 6,221,011 B1 | 4/2001 | Bardy |
| 6,224,566 B1 | 5/2001 | Loeb |
| 6,231,516 B1 | 5/2001 | Keilman et al. |
| 6,235,970 B1 | 5/2001 | Stice et al. |
| 6,237,398 B1 | 5/2001 | Porat et al. |
| 6,238,367 B1 | 5/2001 | Christiansen et al. |
| 6,245,566 B1 | 6/2001 | Gearhart et al. |
| 6,254,573 B1 | 7/2001 | Haim et al. |
| 6,256,233 B1 | 7/2001 | Glass |
| 6,261,230 B1 | 7/2001 | Bardy |
| 6,270,457 B1 | 8/2001 | Bardy |
| 6,277,072 B1 | 8/2001 | Bardy |
| 6,277,078 B1 | 8/2001 | Porat et al. |

| | | |
|---|---|---|
| 6,280,380 B1 | 8/2001 | Bardy |
| 6,284,242 B1 | 9/2001 | Kurachi |
| 6,287,285 B1 | 9/2001 | Michal et al. |
| 6,298,272 B1 | 10/2001 | Peterfeso et al. |
| 6,306,830 B1 | 10/2001 | Hammond et al. |
| 6,309,370 B1 | 10/2001 | Haim et al. |
| 6,312,378 B1 | 11/2001 | Bardy |
| 6,316,419 B1 | 11/2001 | Leiden et al. |
| 6,330,481 B1 | 12/2001 | Van Wijk et al. |
| 6,331,160 B1 | 12/2001 | Bardy |
| 6,336,903 B1 | 1/2002 | Bardy |
| 6,358,202 B1 | 3/2002 | Arent |
| 6,358,203 B2 | 3/2002 | Bardy |
| 6,361,522 B1 | 3/2002 | Scheiner et al. |
| 6,361,780 B1 | 3/2002 | Ley et al. |
| 6,368,284 B1 | 4/2002 | Bardy |
| 6,385,491 B1 | 5/2002 | Lindemans et al. |
| 6,388,043 B1 | 5/2002 | Langer et al. |
| 6,398,728 B1 | 6/2002 | Bardy |
| 6,399,300 B1 | 6/2002 | Field |
| 6,410,236 B1 | 6/2002 | Metzger |
| 6,411,840 B1 | 6/2002 | Bardy |
| 6,424,847 B1 | 7/2002 | Mastrototaro et al. |
| 6,428,802 B1 | 8/2002 | Atala |
| 6,436,672 B1 | 8/2002 | Tomlinson |
| 6,436,907 B1 | 8/2002 | Leiden et al. |
| 6,440,066 B1 | 8/2002 | Bardy |
| 6,443,949 B2 | 9/2002 | Altman |
| 6,451,594 B1 | 9/2002 | Chien et al. |
| 6,453,195 B1 | 9/2002 | Thompson |
| 6,459,917 B1 | 10/2002 | Gowda et al. |
| 6,459,929 B1 | 10/2002 | Hopper et al. |
| 6,463,323 B1 | 10/2002 | Conrad et al. |
| 6,463,335 B1 | 10/2002 | Munch et al. |
| 6,468,263 B1 | 10/2002 | Fischell et al. |
| 6,468,985 B1 | 10/2002 | Huang |
| 6,475,232 B1 | 11/2002 | Babbs et al. |
| 6,478,737 B2 | 11/2002 | Bardy |
| 6,490,482 B2 | 12/2002 | Mori et al. |
| 6,501,983 B1 | 12/2002 | Natarajan et al. |
| 6,507,756 B1 | 1/2003 | Heynen et al. |
| 6,511,477 B2 | 1/2003 | Altman et al. |
| 6,518,245 B1 | 2/2003 | Anderson et al. |
| 6,540,725 B1 | 4/2003 | Ponzi |
| 6,541,116 B2 | 4/2003 | Michal et al. |
| 6,571,125 B2 | 5/2003 | Thompson |
| 6,574,507 B1 | 6/2003 | Bonnet |
| 6,575,931 B1 | 6/2003 | Ponzi |
| 6,592,623 B1 | 7/2003 | Bowlin et al. |
| 6,596,745 B2 | 7/2003 | Gall |
| 6,610,716 B2 | 8/2003 | Wagle et al. |
| 6,623,473 B1 | 9/2003 | Ponzi |
| 6,623,474 B1 | 9/2003 | Ponzi |
| 6,628,987 B1 | 9/2003 | Hill et al. |
| 6,628,988 B2 | 9/2003 | Kramer et al. |
| 6,653,291 B1 | 11/2003 | Badylak et al. |
| 6,654,636 B1 | 11/2003 | Dev et al. |
| 6,656,517 B2 | 12/2003 | Michal |
| 6,660,737 B2 | 12/2003 | Almstead et al. |
| 6,662,044 B2 | 12/2003 | Crawford et al. |
| 6,666,826 B2 | 12/2003 | Salo et al. |
| 6,671,558 B1 | 12/2003 | Soykan et al. |
| 6,678,556 B1 | 1/2004 | Nolan et al. |
| 6,689,117 B2 | 2/2004 | Sweeney et al. |
| 6,690,970 B1 | 2/2004 | Taheri et al. |
| 6,693,133 B1 | 2/2004 | Lopaschuk et al. |
| 6,697,669 B2 | 2/2004 | Dev et al. |
| 6,702,777 B2 | 3/2004 | Haim et al. |
| 6,733,996 B2 | 5/2004 | Froehlich et al. |
| 6,735,471 B2 | 5/2004 | Hill et al. |
| 6,748,653 B2 | 6/2004 | Lindemans et al. |
| 6,759,236 B1 | 7/2004 | Fung et al. |
| 6,775,569 B2 | 8/2004 | Mori et al. |
| 6,775,574 B1 | 8/2004 | Soykan et al. |
| 6,783,979 B2 | 8/2004 | Rosen et al. |
| 6,801,805 B2 | 10/2004 | Stokes et al. |
| 6,802,811 B1 | 10/2004 | Slepian |
| 6,810,286 B2 | 10/2004 | Donovan et al. |
| 6,824,561 B2 | 11/2004 | Soykan et al. |
| 6,849,611 B2 | 2/2005 | Rosen et al. |
| 6,855,124 B1 | 2/2005 | Gonzalez et al. |
| 6,902,522 B1 | 6/2005 | Walsh et al. |
| 6,905,476 B2 | 6/2005 | Ponzi |
| 6,919,207 B2 | 7/2005 | Goodman et al. |
| 6,965,798 B2 | 11/2005 | Kim |
| 6,969,382 B2 | 11/2005 | Richter |
| 6,973,349 B2 | 12/2005 | Salo |
| 6,976,982 B2 | 12/2005 | Santini, Jr. et al. |
| 7,029,466 B2 | 4/2006 | Altman |
| 7,031,775 B2 | 4/2006 | Soykan et al. |
| 7,039,462 B2 | 5/2006 | Pastore et al. |
| 7,294,334 B1 | 11/2007 | Michal et al. |
| 7,320,675 B2 | 1/2008 | Pastore et al. |
| 7,567,841 B2 | 7/2009 | Chan |
| 2001/0000802 A1 | 5/2001 | Soykan et al. |
| 2001/0016193 A1 | 8/2001 | Engler |
| 2001/0051148 A1 | 12/2001 | Tremblay |
| 2001/0051787 A1 | 12/2001 | Haller et al. |
| 2001/0055590 A1 | 12/2001 | Kurachi |
| 2002/0001577 A1 | 1/2002 | Haverich et al. |
| 2002/0010492 A1 | 1/2002 | Donovan et al. |
| 2002/0012657 A1 | 1/2002 | Tremblay |
| 2002/0019350 A1 | 2/2002 | Levine et al. |
| 2002/0022022 A1 | 2/2002 | Shi et al. |
| 2002/0022259 A1 | 2/2002 | Lee et al. |
| 2002/0031501 A1 | 3/2002 | Law |
| 2002/0031827 A1 | 3/2002 | Kanno et al. |
| 2002/0032468 A1 | 3/2002 | Hill et al. |
| 2002/0035346 A1 | 3/2002 | Reynolds et al. |
| 2002/0045809 A1 | 4/2002 | Ben-Haim |
| 2002/0048800 A1 | 4/2002 | Gu et al. |
| 2002/0049154 A1 | 4/2002 | Grissom et al. |
| 2002/0055530 A1 | 5/2002 | Neuberger et al. |
| 2002/0055705 A1 | 5/2002 | Talpade et al. |
| 2002/0065243 A1 | 5/2002 | Fung et al. |
| 2002/0072785 A1 | 6/2002 | Nelson et al. |
| 2002/0077311 A1 | 6/2002 | Leiden et al. |
| 2002/0087116 A1 | 7/2002 | Hartlaub |
| 2002/0098167 A1 | 7/2002 | Anversa et al. |
| 2002/0099026 A1 | 7/2002 | Goodman et al. |
| 2002/0099302 A1 | 7/2002 | Bardy |
| 2002/0107553 A1* | 8/2002 | Hill et al. .................. 607/18 |
| 2002/0110910 A1 | 8/2002 | Gwathmey et al. |
| 2002/0115208 A1 | 8/2002 | Mitchell et al. |
| 2002/0124855 A1 | 9/2002 | Chachques |
| 2002/0127210 A1 | 9/2002 | Mickle et al. |
| 2002/0133198 A1 | 9/2002 | Kramer et al. |
| 2002/0142457 A1 | 10/2002 | Umezawa et al. |
| 2002/0147172 A1 | 10/2002 | Podsakoff et al. |
| 2002/0147329 A1 | 10/2002 | Luyten et al. |
| 2002/0155101 A1 | 10/2002 | Donahue et al. |
| 2002/0161410 A1* | 10/2002 | Kramer et al. ................. 607/9 |
| 2002/0169485 A1 | 11/2002 | Pless et al. |
| 2002/0172663 A1 | 11/2002 | Palasis et al. |
| 2002/0183682 A1 | 12/2002 | Darvish et al. |
| 2002/0183686 A1 | 12/2002 | Darvish et al. |
| 2002/0183720 A1 | 12/2002 | Hill et al. |
| 2003/0004403 A1 | 1/2003 | Drinan et al. |
| 2003/0026784 A1 | 2/2003 | Koch et al. |
| 2003/0036773 A1* | 2/2003 | Whitehurst et al. ............ 607/3 |
| 2003/0040777 A1 | 2/2003 | Shemer et al. |
| 2003/0044802 A1 | 3/2003 | Sayler et al. |
| 2003/0045830 A1 | 3/2003 | de Bizemont et al. |
| 2003/0059463 A1 | 3/2003 | Lahtinen |
| 2003/0060854 A1 | 3/2003 | Zhu |
| 2003/0065379 A1 | 4/2003 | Babbs et al. |

| | | |
|---|---|---|
| 2003/0073235 A1 | 4/2003 | Lagarias et al. |
| 2003/0082148 A1 | 5/2003 | Ludwig et al. |
| 2003/0087867 A1 | 5/2003 | Vogels et al. |
| 2003/0104568 A1 | 6/2003 | Lee |
| 2003/0105493 A1 | 6/2003 | Salo |
| 2003/0113303 A1 | 6/2003 | Schwartz |
| 2003/0125615 A1 | 7/2003 | Schwartz |
| 2003/0129750 A1 | 7/2003 | Schwartz |
| 2003/0130581 A1 | 7/2003 | Salo et al. |
| 2003/0138415 A1 | 7/2003 | Shepard |
| 2003/0144702 A1 | 7/2003 | Yu et al. |
| 2003/0144703 A1 | 7/2003 | Yu et al. |
| 2003/0148351 A1 | 8/2003 | Henry et al. |
| 2003/0148968 A1 | 8/2003 | Hammond et al. |
| 2003/0149420 A1 | 8/2003 | Richter |
| 2003/0153952 A1* | 8/2003 | Auricchio et al. ............... 607/9 |
| 2003/0158584 A1 | 8/2003 | Cates |
| 2003/0167081 A1* | 9/2003 | Zhu et al. .................... 607/122 |
| 2003/0171723 A1 | 9/2003 | Ponzi |
| 2003/0187396 A1 | 10/2003 | Ponzi |
| 2003/0187490 A1 | 10/2003 | Gliner |
| 2003/0195470 A1 | 10/2003 | Ponzi |
| 2003/0204206 A1 | 10/2003 | Padua et al. |
| 2003/0216476 A1 | 11/2003 | Kleemann |
| 2003/0216811 A1 | 11/2003 | Badylak |
| 2003/0216812 A1 | 11/2003 | Badylak |
| 2004/0002739 A1 | 1/2004 | Cates et al. |
| 2004/0006395 A1 | 1/2004 | Badylak |
| 2004/0018174 A1 | 1/2004 | Palasis |
| 2004/0030379 A1 | 2/2004 | Hamm et al. |
| 2004/0038400 A1 | 2/2004 | Froehlich et al. |
| 2004/0043006 A1 | 3/2004 | Badylak et al. |
| 2004/0047909 A1 | 3/2004 | Ragheb et al. |
| 2004/0048286 A1 | 3/2004 | Lee |
| 2004/0049235 A1 | 3/2004 | Deno et al. |
| 2004/0087019 A1 | 5/2004 | Soykan et al. |
| 2004/0098075 A1 | 5/2004 | Lee |
| 2004/0106954 A1* | 6/2004 | Whitehurst et al. ............. 607/3 |
| 2004/0131601 A1 | 7/2004 | Epstein et al. |
| 2004/0132184 A1 | 7/2004 | Dennis et al. |
| 2004/0158289 A1 | 8/2004 | Girouard et al. |
| 2004/0158290 A1 | 8/2004 | Girouard et al. |
| 2004/0161421 A1 | 8/2004 | Komowski et al. |
| 2004/0186546 A1* | 9/2004 | Mandrusov et al. ......... 607/122 |
| 2004/0208845 A1 | 10/2004 | Michal et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2004/0215253 A1 | 10/2004 | Weinberg |
| 2004/0230274 A1 | 11/2004 | Heil et al. |
| 2004/0253209 A1 | 12/2004 | Soykan et al. |
| 2005/0002912 A1 | 1/2005 | Chachques |
| 2005/0005923 A1 | 1/2005 | Herrin |
| 2005/0008628 A1 | 1/2005 | Feld et al. |
| 2005/0013870 A1 | 1/2005 | Freyman et al. |
| 2005/0021091 A1 | 1/2005 | Laske et al. |
| 2005/0025752 A1 | 2/2005 | Kutryk et al. |
| 2005/0043675 A1 | 2/2005 | Pastore et al. |
| 2005/0059153 A1 | 3/2005 | George et al. |
| 2005/0059999 A1 | 3/2005 | Mongeon et al. |
| 2005/0096701 A1 | 5/2005 | Donovan et al. |
| 2005/0112759 A1 | 5/2005 | Radisic et al. |
| 2005/0113705 A1 | 5/2005 | Fischell et al. |
| 2005/0118144 A1 | 6/2005 | Zhang |
| 2005/0130136 A1 | 6/2005 | Lee |
| 2005/0137626 A1* | 6/2005 | Pastore et al. ................. 607/3 |
| 2005/0137631 A1 | 6/2005 | Yu et al. |
| 2005/0137671 A1 | 6/2005 | Liu et al. |
| 2005/0192637 A1 | 9/2005 | Girouard et al. |
| 2005/0245972 A1* | 11/2005 | Onyekaba et al. ............... 607/5 |
| 2005/0283197 A1 | 12/2005 | Daum et al. |
| 2006/0015146 A1 | 1/2006 | Girouard et al. |
| 2006/0036126 A1 | 2/2006 | Ross et al. |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2007/0027487 A1 | 2/2007 | Mika et al. |
| 2007/0054871 A1 | 3/2007 | Pastore et al. |
| 2008/0091138 A1 | 4/2008 | Pastore et al. |

FOREIGN PATENT DOCUMENTS

| | | |
|---|---|---|
| EP | 0467695 A2 | 1/1992 |
| EP | 0545628 A2 | 6/1993 |
| EP | 633031 | 1/1995 |
| EP | 1050265 | 11/2000 |
| EP | 1142607 A2 | 10/2001 |
| WO | WO-9640195 | 12/1996 |
| WO | WO-97/33513 | 9/1997 |
| WO | WO-98/02150 | 1/1998 |
| WO | WO-9802040 A1 | 1/1998 |
| WO | WO-9802150 A1 | 1/1998 |
| WO | WO-9815317 A1 | 4/1998 |
| WO | WO-9834537 A1 | 8/1998 |
| WO | WO-9904851 | 2/1999 |
| WO | WO-9925385 A1 | 5/1999 |
| WO | WO-9936563 | 7/1999 |
| WO | WO-0007497 A1 | 2/2000 |
| WO | WO-0017326 | 3/2000 |
| WO | WO-0027466 A1 | 5/2000 |
| WO | WO-0054661 A1 | 9/2000 |
| WO | WO-0062855 A1 | 10/2000 |
| WO | WO-0074584 | 12/2000 |
| WO | WO-0074773 A1 | 12/2000 |
| WO | WO-0103750 | 1/2001 |
| WO | WO-0204063 A1 | 1/2002 |
| WO | WO-0205866 A2 | 1/2002 |
| WO | WO-0249669 A2 | 6/2002 |
| WO | WO-0249714 A2 | 6/2002 |
| WO | WO-02070065 A2 | 9/2002 |
| WO | WO-02087681 A2 | 11/2002 |
| WO | WO-2004016200 | 2/2004 |
| WO | WO-2004024206 | 3/2004 |
| WO | WO-2004/030706 | 4/2004 |
| WO | WO-2004026394 A1 | 4/2004 |
| WO | WO-2004030706 | 4/2004 |
| WO | WO-2004050180 A2 | 6/2004 |
| WO | WO-2004080533 A1 | 9/2004 |
| WO | WO-2004093969 A1 | 11/2004 |
| WO | WO-2005084751 A2 | 9/2005 |
| WO | WO-2005084751 A3 | 9/2005 |
| WO | WO-2005120635 A1 | 12/2005 |
| WO | WO-2006019856 A1 | 2/2006 |

OTHER PUBLICATIONS

Brunner, Friedrich, "Attenuation of myocardial ischemia/reperfusion injury in mice with myocyte-specific overexpression of endothelial nitric oxide synthase", *Cardiovascular Research*, 57, (2003), 55-62.

Colonna, P., et al., "Myocardial infarction and left ventricular remodeling: results of the CEDIM trial. Carnitine Ecocardiografia Digitalizzata Infarto Mio", *Am Heart J.*, 139(2 Pt 3), (Feb. 2000), S124-30.

Freedman, Saul B., et al., "Therapeutic Angiogenesis for Ischemic Cardiovascular Disease", *J. Mol Cell Cardiol.*, 33(3), (Mar. 2001), 379-393.

Graham, Regina M., et al., "Gene and Cell Therapy for Heart Disease", *IUBMB Life*, 54, (2002), 59-66.

Hakuno, Daihiko, et al., "Bone Marrow-Derived Regenerated Cardiomyocytes (CMG Cells) Express Functional Adrenergic and Muscarinic Receptors", *Circulation*, 105, (Jan. 22, 2002), 380-386.

Hamawy, A. H., et al., "Cardiac Angiogenesis and Gene Therapy: A Strategy for Myocardial Revascularization", *Current Opinion in Cardiology*, 14, (1999), 515-522.

Harjai, Kishore J., et al., "Therapeutic Angiogenesis: a Fantastic New Adventure", *Journal of Interventional Cardiology*, 15 (3), (2002), 223-229.

Hodde, Jason P., et al., "Retention of Endothelial Cell Adherence to Porcine-Derived Extracellular Matrix After Disinfection and Sterilization", *Tissue Engineering*, 8(2), (Apr. 2002), 225-34.

Ingber, Donald E., "Mechanical signaling and the cellular response to extracellular matrix in angiogenesis and cardiovascular physiology", *Circulation Research*, 91(10), (Nov. 15, 2002), 877-87.

Isner, Jeffrey M., "Myocardial gene therapy", *Nature*, 415(6868), (Jan. 10, 2002), 234-239.

Jackson, K. A., "Regeneration of Ischemic Cardiac Muscle and Vascular Endothelium By Adult Stem Cells", *The Journal of Clinical Investigation*, 107(11), (Jun. 2001), 1395-1402.

Kocher, A. A., et al., "Neovascularization of Ischemic Myocardium by Human Bone-Marrow-Derived Angioblasts Prevents Cardiomyocyte Apoptosis, Reduces Remodeling and Improves Cardiac Function", *Nature Medicine*, vol. 7. No. 4., (Apr. 2001). pp. 430-436.

Komuro, Issei, et al., "Control of Cardiac Gene Expression by Mechanical Stress", *Annu Rev Physiol.*, 1993, pp. 55-75.

Kozarsky, K. F., "Gene Therapy for Cardiovascular Disease", *Current Opinion in Pharmacology*, 1, (2001), 197-202.

Losordo, Douglas W., et al., "Gene Therapy for Myocardial Angiogenesis", *Am Heart J.*, vol. 138., (1999), pp. S132-S141.

Mann, Brenda K., et al., "Tissue engineering in the cardiovascular system: progress toward a tissue engineered heart", *The Anatomical Record*, 263(4), (Aug. 1, 2001), 367-371.

Miyagawa, Shigeru, et al., "Myocardial Regeneration Therapy for Heart Failure: Hepatocyte Growth Factor Enhances The Effect of Cellular Cardiomyoplasty", *Circulation*, 105(21), (May 28, 2002), 2556-2561.

Nemer, Georges, et al., "Regulation of Heart Development and Function Through Combinatorial Interactions of Transcription Factors", *The Finnish Medical Society Duodecim, Ann Med*, vol. 33., (2001), pp. 604-610.

Orlic, D., et al., "Bone Marrow Cells Regenerate Infarcted Myocardium", *Nature*, 410, (Apr. 5, 2001), 701-705.

Pastore, Joseph M., et al., "Method and Apparatus for Device Controlled Gene Expression for Cardiac Protection", U.S. Appl. No. 11/220,397, filed Sep. 6, 2005, 68 Pgs.

Pasumarthi, Kishore B., et al., "Cardiomyocyte Cell Cycle Regulation", *Circ Res.*, 90(10), (2002), 1044-1054.

Reinecke, Hans, et al., "Survival, integration, and differentiation of cardiomyocyte grafts: a study in normal and injured rat hearts", *Circulation*, 100(2), (1999), 193-202.

Ross, Jeffrey, "Epicardial Patch Including Isolated Extracellular Matrix With Pacing Electrodes", U.S. Appl. No. 11/017,627, filed Dec. 20, 2004, 87 pgs.

Ross, Jeffrey, et al., "Use of Extracellular Matrix and Electrical Therapy", U.S. Appl. No. 11/017,237, filed Dec. 20, 2004, 89 pgs.

Taylor, Doris A., et al., "Regenerating Functional Myocardium: Improved Performance after Skeletal Myoblast Transplantation", *Nature Medicine*, 4(8), (Aug. 1998), 929-933.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41. No. 3, (Mar. 2003), 474-480.

Wunderlich, Carsten, "Acute Inhibition of Myoglobin Impairs Contractility and Energy State of iNOS-Overexpressing Hearts", *Circulation Research*, 92, (2003), 1352-1358.

"International Search Report and Written Opinion for Application No. PCT/US2005/019731, date mailed Oct. 6, 2005", 15 Pages.

Akiyama-Uchida, Y., et al., "Norepinephrine enhances fibrosis mediated by TGF-beta in cardiac fibroblasts", *Hypertension*, 40(2), (Aug. 2002),148-54.

Aukrust, Pal, et al., "Immunomodulating Therapy: New Treatment Modality in Congestive Heart Failure", *Congest Heart Fail.*, 9(2), (Mar.-Apr. 2003),64-69.

Bigatel, D. A., et al., "The matrix metalloproteinase inhibitor BB-94 limits expansion of experimental abdominal aortic aneurysms", *J Vasc Surg*, 29(1), (1999),130-8.

Capecchi, M. R., "High efficiency transformation by direct microinjection of DNA into cultured mammalian cells.", *Cell*, 22(2 Pt 2), (Nov. 1980),479-88.

Chu, G., et al., "SV40 DNA transfection of cells in suspension: analysis of efficiency of transcription and translation of T-antigen.", *Gene*, 13(2), (Mar. 1981), 197-202.

Colucci, Wilson S., "Molecular and Cellular Mechanisms of Myocardial Failure", *Am J Cardiol* 80(11A), (1997),15L-25L.

Cserjesi, P., et al., "Myogenin induces the myocyte-specific enhancer binding factor MEF-2 independently of other muscle-specific gene products", *Mol Cell Biol*, 11(10), (Oct. 1991), 4854-62.

Curiel, D. T., et al., "Adenovirus enhancement of transferrin-polylysine-mediated gene delivery", *Proc Natl Acad SCI USA.*, 88(19), (Oct. 1, 1991),8850-4.

Dhawan, J., et al., "Tetracycline-regulated gene expression following direct gene transfer into mouse skeletal muscle", *Somat Cell Mol Genet.*, 21(4), (1995),233-40.

Eckardt, Lars, et al., "Load-induced changes in repolarization: evidence from experimental and clinical data", *Basic Res Cardiol*, 96(4), (2001),369-380.

Cate, F. U., et al., "Endocardial and epicardial steorid lead pacing in the neonantal and paediatric age group", *Heart*, 88.www.heartjnl.com, (2002),392-396.

De Silva, R., et al., "Delivery and tracking of therapeutic cell preparations for clinical cardiovascular applications", *Cytotherapy*, 6(6), (2004),608-614.

Cohen, Mitchell I., et al., "Permanent epicardial pacing in pediatric patients: seventeen years of experience and 1200 outpatient visits.", *Circulation*, 103(21), (2001), 2585-2590.

Conley, B. J., et al., "Derivation, propagation and differentiation of human embryonic stem cells", *The International Journal of Biochemistry & Cell Biology*, 36, (2004), 555-567.

Eck, S., et al., "Gene-Based Therapy", *Goodman & Gilman's The Pharmacological Basis of Therapeutics, Chapter 5, Section 1, General Principles*, New York; McGraw-Hill, (2001), 77-101.

Elisseeff, Jennifer, et al., "Controlled-release of IGF-I and TGF-B1 in a photopolymerizing Hydrogel for cartilage tissue engineering", *Journal of Orthopaedic Research*, vol. 19, (2001), 1098-1104.

Gage, H. F., "Cell Therapy", *Nature*, 392, Supp., (Apr. 28, 1998), 18-24.

Kofidis, T., et al., "In vitro engineering of heart muscle: Artificial myocardial tissue", *The Journal of Thoracic and Cardiovascular Surgery*, 124 (1), (2002) 63-69.

Odorico, S. J., et al., "Multilineage differentiation from human embryonic stem cell lines", *Stem Cells*, 19(3), (2001),193-204.

Parikh, S., et al., "Endothelial Cell Delivery for Cardiovascular Therapy", *Advanced Drug Delivery Reviews*, 42, (2000), 139-161.

Pfeifer, A., et al., "Gene Therapy: Promises and Problems", *Ann. Rev. of Genomics and Hum. Genet.*, 2, (2001), 177-211.

Samstein, B., et al., "Physiologic and Immunologic Hurdles to Xenotransplantation", *Journal of the American Society of Nephrology*, 12, (2001), 182-193.

Srour, E. F., et al., "Ex Vivo Expansion of Hematopoietic Stem and Progenitor Cells: Are We There Yet?", *The Journal of Hematotherapy*, 8, (1999), 93-102.

Stolen, Craig, et al., "Method and Apparatus for Preconditioning of Cells", U.S. Appl. No. 11/424,066, filed Jun. 14, 2006, 36 Pages.

Verma, I. M., et al., "Gene Therapy—Promises, Problems and Prospects",*Nature*, 389, (Sep. 18, 1997), 239-242.

Felgner, P. L., "Lipofection: A highly efficient, lipid-mediated DNA-transfection procedure", *Proceedings of the National Academy of Sciences*, 84, Biochemistry,(Nov. 1987),pp. 7413-7417.

Graham, F. L., "A New Technique for the Assay of Infectivity of Human Adenovirus 5 DNA", *Virology*, 52, (1973),456-467.

Hafizi, S., et al., "Inhibition of human cardiac fibroblast mitogenesis by blockade of mitogen-activated protein kinase and phosphatidylinositol 3-kinase.", *Cir Exp Pharma Physiol*, 26(7), (Jul. 1999),511-3.

Hammond, H. K., et al., "Regional myocardial downregulation of the inhibitory guanosine triphosphate-binding protein (Gi alpha 2) and beta-adrenergic receptors in a porcine model of chronic episodic myocardial ischemia", *J Clin Res*, 92(6), (1993),2644-52.

Higashi, T., et al., "Pharmacological characterization of endothelin-induced rat pulmonary arterial dilatation", *Br J Pharmacol*, 121(4), (1997),782-6.

Jain, Mohit, et al., "Cell therapy attenuates deleterious ventricular remodeling and improves cardiac performance after myocardial Infarction", *Circulation*, 103(14), (Apr. 10, 2001),1920-1927.

Johnson, J. E., et al., "Muscle creatine kinase sequence elements regulating skeletal and cardiac muscle expression in transgenic mice", *Mol Cell Biol.*, 9(8), (1989),3393-9.

Jugdutt, Bodh I., "Remodeling of the Myocardium and Potential Targets in the Collagen Degradation and Synthesis Pathways", *Current Drug Targets Cardiovascular & Haematological Disorders*, 3, (2003),1-30.

Kiba, A., et al., "VEGFR-2-specific ligand VEGF-E induces non-edematous hyper-vascularization in mice.", *Biochem Biophys Res Commun.*, 301(2), (Feb. 7, 2003),371-7.

Klein, T. M., "High-Velocity Microprojectiles for Delivering Nucleic Acids into Living Cells", *Nature*, 327, (1987),70-73.

Kodama, I., et al., "Cellular electropharmacology of amiodarone.", *Cardiovas Res*, 35(1), (1997),13-29.

Lijnen, P. J., et al., "Induction of Cardiac Fibrosis by Transforming Growth Factor-B1", *Molecular Genetics and Metabolism*, 71, (2000),418-435.

Mackenna, Deidre, et al., "Role of mechanical factors in modulating cardia fibroblast function and extracellular matrix synthesis", *Cardiovascular Research*, 46, (2000),257-263.

Mader, S., et al., "A steroid-Inducible promoter for the controlled overexpression of cloned genes in eukaryotic cells", *Proc Natl Acad Sci USA*, 90(12), (1993),5603-7.

Mannino, R. J., et al., "Liposome mediated gene transfer.", *BioTechniques*, 6(7), (Jul.-Aug. 1988),682-90.

Min, Mart, et al., "Electrical Impedance and Cardiac Monitoring-Technology, Potential and Applications", *International Journal of Bioelectromagnetism*, 5(1), (2003),53-56.

Muscat, G. E., et al., "Multiple 5'-flanking regions of the human alpha-skeletal actin gene synergistically modulate muscle-specific expression", *Mol Cell Biol*, 7(11), (1987),4089-99.

Palermo, J., et al., "Transgenic remodeling of the contractile apparatus in the mammalian heart", *Circ Res*, 78(3), (1996),504-9.

Pouleur, H., et al., "Changes in plasma renin activity and haemodynamics during vasodilator therapy in conscious dogs with myocardial infarction or chronic volume overload.", *Eur J Clin Investig*, 13(4), (1983),331-8.

Pouzet, B., et al., "Intramyocardial transplantation of autologous myoblasts: can tissue processing be optimized?", *Circulation*, 102(19 Suppl 3).

Rinsch, C., et al., "Delivery of FGF-2 but not VEGF by encapsulated genetically engineered myoblasts improves survival and vascularization in a model of acute skin flap ischemia", *Gene Therapy*, 8, (2001),523-533.

Roth, D. A., et al., "Downregulation of cardiac guanosine 5'-triphosphate-binding proteins in right atrium and left ventricle in pacing-induced congestive heart failure", *J Clin Invest.*, 91(3), (Mar. 1993),939-49.

Sam, Flora, et al., "Role of Endothelin-1 in Myocardial Failure", *Proceedings of the Association of American Physicians*, 111(5), (1999),417-422.

Semenza, G. L., et al., "Hypoxia-inducible nuclear factors bind to an enhancer element located 3' to the human erythropoietin gen", *Proc Natl Acad Sci USA*, 88(13), (1991),5680-4.

Semenza, G. L., et al., "Transcriptional regulation of genes encoding glycolytic enzymes by hypoxia-inducible factor 1", *J Biol Chem*, 269(38), (1994),23757-63.

Shigekawa, K., "Electroporation of Eukaryotes and Prokaryotes: A General Approach to the Introduction of Macromolecules into Cells", *BioTechniques*, 6, (1988),742-751.

Shockett, P., et al., "A modified tetracycline-regulated system provides autoregulatory, inducible gene expression in cultured cells and transgenic mice", *Proc Natl Acad Sci USA*, 92(14), (1995),6522-6.

Sukenaga, Y., et al., "Development of the chymase inhibitor as an anti-tissue-remodeling drug: myocardial infarction and some other possibilities", *Jap J Pharmacol*, 90(3), (2002),218-22.

Suzuki, Ken, et al., "Cell Transplantation for the Treatment of Acute Myocardial Infarction Using Vascular Endothelial Growth Factor-Expressing Skeletal Myoblasts", *Circulation*: 104[suppl 1], (2001),I-207-I-212.

Taylor, D. A., et al., "Delivery of primary autologous skeletal myoblasts into rabbit heart by coronary infusion: a potential approach to myocardial repair", *Proc Assoc Am Phys*, 109(3), (May 1997),245-53.

Terracio, Louis, et al., "Effects of Cyclic Mechanical Stimulation of the Cellular Components of the Heart: In Vitro.", *In Vitro Cellular & Develomental Biology*, 24(1), (Jan. 1988),53-58.

Villarreal, F. J., et al., "Human cardiac fibroblasts and receptors for angiotensin II and bradykinin: A potential role for bradykinin in the modulation of cardiac extracellular matrix", *Basic research in cardiology*, 93 Supp 3, (1998),s004-s007.

Walter, Dirk H., et al., "Endothelial progenitor cells: regulation and contribution to adult neovascularization", *Herz*, 27(7), (2002),579-588.

Weintraub, H., "The myoD gene family: nodal point during specification of the muscle cell lineage", *Science*, 251(4995), (Feb. 15, 1991),761-6.

Yagi, A., et al., "Anti-inflammatory constituents, aloesin and aloemannan in Aloe species and effects of tanshinon VI in *Salvia miltiorrhiza* on heart", *J Pharm Soc Japan*, 123(7), (Jul. 2003),517-32.

Zimmermann, W. H., et al., "Tissue engineering of a differentiated cardiac muscle construct", *Circulation Res.*, 90(2), (2002),223-30.

"U.S. Appl. No. 10/645,823 Non Final Office Action mailed Mar. 8, 2007", 8 pgs.

"U.S. Appl. No. 10/645,823 Notice of Allowance mailed Aug. 27, 2007", 7 pgs.

"U.S. Appl. No. 10/645,823 Response filed Jun. 8, 2007 to Non Final Office Action mailed Mar. 8, 2007", 19 pgs.

"U.S. Appl. No. 10/742,574, Response filed Sep. 25, 2007 to Final Office Action mailed Aug. 7, 2007", 17 pgs.

"U.S. Appl. No. 10/742,574 Advisory Action Mailed Dec. 21, 2006", 3 pgs.

"U.S. Appl. No. 10/742,574 Supplemetal Amendment & Response filed Jan. 24, 2007 to Final Office Action Mailed Oct. 27, 2006 and Advisory Action dated Dec. 21, 2006", 17 pgs.

"U.S. Appl. No. 10/742,574 Final Office Action mailed Oct. 27, 2006", 14 pgs.

"U.S. Appl. No. 10/742,574 Non Final Office Action mailed Feb. 12, 2007", 13 pgs.

"U.S. Appl. No. 10/742,574 Non Final Office Action mailed May 23, 2006", 11 pgs.

"U.S. Appl. No. 10/742,574 Non-Final Office Action mailed Oct. 17, 2007", 10 pgs.

"U.S. Appl. No. 10/742,574 Response filed May 14, 2007 to Non Final Office Action mailed Feb. 12, 2007", 15 pgs.

"U.S. Appl. No. 10/742,574 Response filed Aug. 23, 2006 to Non Final Office Action mailed May 23, 2006", 17 pgs.

"U.S. Appl. No. 10/742,574 Response filed Dec. 7, 2006 to Final Office Action mailed Oct. 27, 2006", 16 pgs.

"U.S. Appl. No. 10/890,825 Final Office Action mailed Jun. 7, 2007", 10 pgs.

"U.S. Appl. No. 10/890,825 Non Final Office Action mailed Jan. 11, 2007", 8 pgs.

"U.S. Appl. No. 10/890,825 Response filed Apr. 11, 2007 to Non Final Office Action mailed Jan. 11, 2007", 17 pgs.

"U.S. Appl. No. 10/890,825 Response filed Sep. 7, 2007 to Final Office Action mailed Jun. 7, 2007", 22 pgs.

"U.S. Appl. No. 10/890,825, Non-Final Office Action mailed Nov. 20, 2007", 10 pgs.

"U.S. Appl. No. 10/922,650, Final Office Action Mailed Nov. 28, 2007", 13 pgs.

"U.S. Appl. No. 10/922,650 Final Office Action filed Apr. 11, 2007", 11 pgs.

"U.S. Appl. No. 10/922,650 Non Final Office Action filed Jun. 20, 2007", 10 pgs.

"U.S. Appl. No. 10/922,650 Non Final Office Action mailed Sep. 27, 2006", 9 pgs.

"U.S. Appl. No. 10/922,650 Response filed Jan. 25, 2007 to Non Final Office Action mailed Sep. 27, 2006", 15 pgs.

"U.S. Appl. No. 10/922,650 Response filed Jun. 11, 2007 to Final Office Action mailed Apr. 11, 2007", 15 pgs.

"U.S. Appl. No. 10/922,650 Response filed Sep. 19, 2007 to Non Final Office Action mailed Jun. 20, 2007", 17 pgs.

"U.S. Appl. No. 10/925,508 Advisory Action mailed Sep. 27, 2007", 3 pgs.

"U.S. Appl. No. 10/925,508 Final Office Action mailed Jul. 23, 2007", 10 pgs.

"U.S. Appl. No. 10/925,508 Non Final Office Action mailed Feb. 14, 2007", 11 pgs.

"U.S. Appl. No. 10/925,508 Response filed May 10, 2007 to Non Final Office Action mailed Feb. 14, 2007", 19 pgs.

"U.S. Appl. No. 10/925,508 Response filed Sep. 19, 2007 to Final Office Action mailed Jul. 23, 2007", 18 pgs.

"U.S. Appl. No. 10/742,574, Response filed Jan. 17, 2008 to Non-Final Office Action mailed Oct. 17, 2007", 17 pgs.

"U.S. Appl. No. 10/742,574 Final Office Action mailed May 9, 2008", 13pgs.

"U.S. Appl. No. 10/890,825, Response filed Feb. 20, 2008 to Non-Final Office Action mailed Nov. 20, 2007", 20 pgs.

"U.S. Appl. No. 10/890,825, Non-Final Office Action mailed May 13, 2008", 10 pgs.

"U.S. Appl. No. 10/919,016, Non-Final Office Action mailed Jan. 18, 2008", 21 pgs.

"U.S. Appl. No. 10/919,016 Response filed Apr. 18, 2008 to Non-Final Office Action mailed Jan. 18, 2008", 12 pages.

"U.S. Appl. No. 10/922,650, Response filed Jan. 28, 2008 to Final Office Action mailed Nov. 28, 2007", 17 pgs.

"U.S. Appl. No. 10/922,650, Response filed Mar. 28, 2008 to Final Office Action mailed Nov. 28, 2007", 17 pgs.

"U.S. Appl. No. 10/925,508 Non-final office action mailed Jan. 17, 2008", 11 Pages.

"U.S. Appl. No. 10/925,508, Response filed Apr. 17, 2008 to Non-Final Office Action mailed Jan. 17, 2008", 13 pgs.

Chachques, J. C., et al., "Electrostimulation Enhanced Fatigue Resistant Myosin Expression in Cellular Cardiomyoplasty", *Circulation*, 104(*Suppl.2*), (Abstract No. 2626), Abstracts from Scientific Sessions 2001, Anaheim, CA, Nov. 11-14, 2001, (2001),II-555-II-556.

Kaye, et al., "Role of Tansiently altered sarcolemmal membrane permeability and basic fribroblast growth factor release . . .", *J.Clin. Invest.* vol. 97, (1996),281-291.

Pratt, A. B., et al., "Synthetic Extracellular Matrices for in situ Tissue Engineering", *Biotechnology and Bioengineering*, 86(1), (2004),27-36.

Shimizu, T., et al., "Electrically Communicating Three-Dimensional Cardiac Tissue Mimic Fabricated by Layered Cultured Cardiomyocyte Sheets", *J. Biomedical Materials Research*, 60, (2004),110-117.

Willey, C. D., et al., "Focal Complex Formation in Adult Cardiomyocytes is Accompanied by the Activation of Beta3 Integrin and c-Src", *Journal of Molecular and Cellular Cardiology*, 35, (2003),671-683.

Yamamoto, et al., "Regulation of cardiomyocyte mechanotransduction by the cardiac cycle", *Circulation.* vol. 103 (2001),1459-1464.

Yao, M., et al., "Long-Term Outcome of Fetal Cell Transplantation on Postinfarction Ventricular Remodeling and Function", *Journal of Molecular and Cellular Cardiology*, 35, (2003),661-670.

Zimmermann, W.-H., et al., "Engineered Heart Tissue for Regeneration of Diseased Hearts", *Biomaterials*, 25, (2004),1639-1647.

"U.S. Appl. No. 10/742,574, Response filed Dec. 22, 2008 to Non Final Office Action mailed Oct. 2, 2008", 11 pgs.

"U.S. Appl. No. 10/925,508 Non-Final Office Action mailed Jan. 6, 2009", 8 pgs.

"U.S. Appl. No. 10/922,650 Final Office Action mailed Dec. 22, 2008", 10 pgs.

"U.S. Appl. No. 10/742,574, Advisory Action mailed Apr. 24, 2009", 3 pgs.

"U.S. Appl. No. 10/742,574, Final Office Action mailed Jan. 15, 2010", 12 pgs.

"U.S. Appl. No. 10/742,574, Final Office Action mailed Feb. 18, 2009", 11 pgs.

"U.S. Appl. No. 10/742,574, Non-Final Office Action mailed May 28, 2009", 12 pgs.

"U.S. Appl. No. 10/742,574, Response filed Apr. 20, 2009 to Final Office Action mailed Feb. 18, 2009", 11 pgs.

"U.S. Appl. No. 10/742,574, Response filed Sep. 28, 2009 to Non Final Office Action mailed May 28, 2009", 11 pgs.

"U.S. Appl. No. 10/890,825, Final Office Action mailed Jun. 22, 2009", 14 pgs.

"U.S. Appl. No. 10/890,825, Notice of Allowance mailed Jan. 19, 2010", 7 pgs.

"U.S. Appl. No. 10/890,825, Response filed Feb. 23, 2009 to Non Final Office Action mailed Nov. 14, 2008", 22 pgs.

"U.S. Appl. No. 10/890,825, Response filed Nov. 6, 2009 to Final Office Action mailed Jun. 22, 2009", 24 pgs.

"U.S. Appl. No. 10/922,650, Advisory Action mailed Feb. 19, 2008", 3 pgs.

"U.S. Appl. No. 10/922,650, Notice of Allowance mailed Mar. 31, 2009", 7 pgs.

"U.S. Appl. No. 10/922,650, Response filed Feb. 23, 2009 to Final Office Action mailed Dec. 22, 2008", 8 pgs.

"European Application No. 05757159.8, Communication mailed Mar. 16, 2007", 2 pgs.

"European Application No. 05757159.8, Office Action received Oct. 29, 2009", 3 pgs.

"European Application No. 05757159.8, Response filed Apr. 24, 2007 to Communication mailed Mar. 16, 2007", 16 pgs.

US 6,875,206, 04/2005, Ponzi (withdrawn)

* cited by examiner

METHOD AND APPARATUS TO MODULATE CELLULAR REGENERATION POST MYOCARDIAL INFARCT

CROSS-REFERENCE TO RELATED APPLICATION

This application is related to co-pending, commonly assigned U.S. patent application Ser. No. 10/645,823, entitled "METHOD AND APPARATUS FOR MODULATING CELLULAR METABOLISM DURING POST-ISCHEMIA OR HEART FAILURE," filed on Aug. 21, 2003, which is hereby incorporated by reference in its entirety.

BACKGROUND OF THE INVENTION

The heart is the center of a person's circulatory system. It includes an electromechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. The efficiency of the pumping functions, indicative whether the heart is normal and healthy, is indicated by measures of hemodynamic performance, such as parameters related to intracardiac blood pressures and cardiac output.

In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply. The adult heart lacks a substantial population of precursor, stem cells, or regenerative cells. Therefore, after MI, the heart lacks the ability to effectively regenerate cardiomyocytes to replace the injured cells in the infarcted areas of the myocardium. Each injured area eventually becomes a fibrous scar that is non-conductive and non-contractile. Consequently, the overall contractility of the myocardium is weakened, resulting in decreased cardiac output. As a physiological compensatory mechanism that acts to increase cardiac output in response to MI, the LV diastolic filling pressure increases as the pulmonary and venous blood volume increases. This increases the LV preload (stress on the LV wall before its contracts to eject blood). One consequence is the progressive change of the LV shape and size, a processes referred to as remodeling. Remodeling is initiated in response to a redistribution of cardiac stress and strain caused by the impairment of contractile function in the infarcted tissue as well as in nearby and/or interspersed viable myocardial tissue with lessened contractility due to the infarct. The remodeling starts with expansion of the region of the infarcted tissue and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, post MI patients experience impaired hemodynamic performance and have a significantly increased risk of developing heart failure.

What is needed is a method with long term effectiveness in treating myocardial injuries after MI.

SUMMARY OF THE INVENTION

The invention provides a system coupled to a heart having a myocardial infarct region. The system includes an implantable agent delivery device adapted to contain one or more agents that modulate myocardial tissue growth and to release the one or more agents to a cardiac region including at least portions of the myocardial infarct region, and an implantable cardiac rhythm management (CRM) device including a pacing circuit to deliver pacing pulses to the cardiac region, and a pacing controller adapted to control the delivery of the pacing pulses to enhance the modulation of myocardial tissue growth by the one or more agents.

Also provided is a method for modulating tissue growth in a myocardial infarct region. The method includes delivering (applying) one or more agents to a cardiac region including at least portions of the myocardial infarct region in an amount effective to modulate myocardial tissue growth, and delivering pacing pulses to the cardiac region to enhance the modulation of the myocardial tissue growth by the one or more agents.

Further provided is a method for modulating scar formation at a site of myocardial injury in an animal. The method includes delivering pacing pulses and administering one or more agents that modulate fibrosis to an animal having a myocardial injury. The pacing pulses are delivered to cardiac tissue so as to reduce cardiac wall stress or workload, and the at least one agent is administered in an amount effective to modulate fibrosis scarring at a site of myocardial injury.

In another embodiment, the invention provides a method for enhancing replacement of tissue at a site of myocardial injury in an animal. The method includes delivering pacing pulses and administering one or more agents that promote stem cell migration (localization), implantation and/or proliferation to an animal having a myocardial injury. The pacing pulses are delivered to cardiac tissue so as to reduce cardiac wall stress or workload, and the at least one agent is administered in an amount effective to enhance stem cell migration, implantation and/or proliferation at a site of myocardial injury.

An agent employed in a system or method of the invention includes one or more agents that modulate myocardial tissue growth after myocardial injury, e.g., agents that alter wound healing or tissue replacement, for instance, after post-myocardial infarction. The injury may be due to an invasive procedure, e.g., surgery, or a result of a cardiovascular condition. The one or more agents are administered in an amount effective to enhance the mechanical properties or vascularization of the heart (e.g., increased blood vessel formation in the heart), decrease adverse remodeling of the heart, modulate fibrosis in the heart, and/or enhance migration, implantation or proliferation of stem cells in the heart, or any combination thereof. Thus, in one embodiment, administration of the one or more agents decreases the extent of scar formation associated with fibrosis and/or increases the number of living cells at or near a site of injury. In one embodiment, administration of one or more agents of the invention may result in a healing process that is favorable for ventricular remodeling. In another embodiment, the one or more agents enhance the regeneration of myocardium, e.g., functional myocardium, at the site of injury.

In one embodiment, the agents of the invention are biological agents, i.e., those found in and/or expressed by wild-type cells, which agents may be delivered as proteins, glycoproteins, proteoglycans, and the like, or as a vector which comprises at least a portion of a gene which encodes a protein, glycoprotein, or proteoglycan component. If the agent is a protein, it may be a recombinant protein, including a fusion protein. In addition, the agents of the invention may be employed in conjunction with other therapies, e.g., therapies for ischemia or arrhythmias, including gene therapies and/or cell therapies.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document. The drawing are for illustrative purposes only and not to scale nor anatomically accurate.

DETAILED DESCRIPTION OF THE INVENTION

Figure 1:
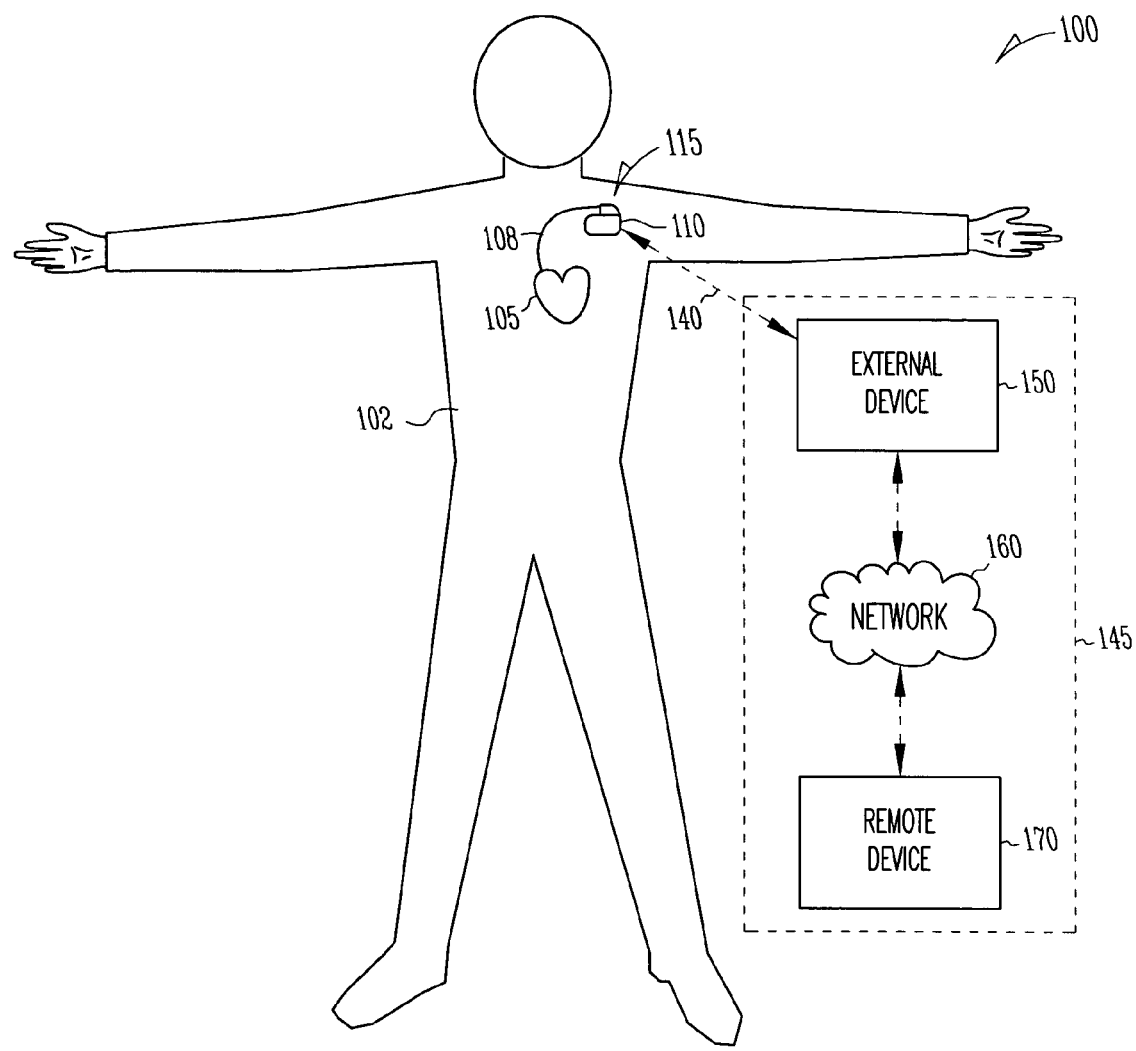
FIG. 1 is an illustration of an embodiment of a system delivering combined electrical and agent therapies a heart and portions of an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

Definitions

A "cytokine" is a relatively low molecular weight protein secreted by cells, e.g., cells of the immune system, for the purpose of altering the function(s) of those cells and/or adjacent cells. Cytokines include interleukins, e.g., molecules which regulate the inflammatory and immune response, as well as growth and colony stimulating factors.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, recombinant viral vectors (such as recombinant adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source, or to cells which have not been genetically modified, i.e., nonrecombinant cells. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector, e.g., a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer element" is meant a nucleic acid sequence that, when positioned proximate to a promoter, confers increased transcription activity relative to the transcription activity resulting from the promoter in the absence of the enhancer domain. By "cardiac-specific enhancer element" is meant an element, which, when operably linked to a promoter, directs gene expression in a cardiac cell and does not direct gene expression in all tissues or all cell types. Cardiac-specific enhancers of the present invention may be naturally occurring or non-naturally occurring. One skilled in the art will recognize that the synthesis of non-naturally occurring enhancers can be performed using standard oligonucleotide synthesis techniques.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" as used herein includes vertebrates such as avians, amphibians, reptiles, fish and other aquatic organisms.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide or polypeptide or cell refers to a nucleic acid sequence, peptide, polypeptide or cell that is identified and separated from at least one contaminant nucleic acid, polypeptide or other biological component with which it is ordinarily associated in its natural source. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and "protein" are used interchangeably herein unless otherwise distinguished.

By "growth factor" is meant an agent that, at least, promotes cell growth or induces phenotypic changes.

The term "angiogenic growth factor" means an agent that alone or in combination with other agents induces angiogenesis, and includes, but is not limited to, fibroblast growth factor (FGF), vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (G-CSF), placental GF, IL-8, proliferin, angiopoietin, e.g., angiopoietin-1 and angiopoietin-2, thrombospondin, ephrin-A1, E-selectin, leptin and heparin affinity regulatory peptide.

The term "agents," as used in this document, include agents that are chemical and/or biological in origin.

As used herein, "vascularization" (formation of vessels that are capable of conducting fluid) includes vasculogenesis and angiogenesis. Vasculogenesis is the organization of undifferentiated endothelial cells into vascular structures. Vasculogenesis may be followed by angiogenesis, whereby previously formed vessels extend into undervascularized regions. During angiogenesis, endothelial cells proliferate and extend from previously formed vessels, forming new vascular structures.

General Overview

This document describes, among other things, method and apparatus for agent therapy and electrical therapy of myocardial tissue, e.g., tissue which has been injured. In one embodiment, agent therapy is applied to tissue by locally administering to a recipient animal, e.g., a mammal, one or more agents, e.g., protein, glycoprotein, peptide, or a vector, to tissue in vivo. In one embodiment, the area including the damaged tissue is subjected to electrical and agent therapy while in other embodiments the tissue is subjected to electrical therapy, agent therapy and cell therapy, e.g., inserting or applying, appropriate cellular material ("donor cells") into and/or to the tissue. The donor cells may be ones expanded ex vivo, including those subjected to in vitro conditioning as described below, including those which are genetically modified.

Electrical therapy may be applied before, during, or after agent therapy, or any combination thereof. In one embodiment, agent administration is for a period of time during electrical therapy. In another embodiment, agent administration is initiated before electrical therapy and optionally continues for a period during electrical therapy. In another embodiment, an agent is administered, then electrical therapy is initiated. In one approach, donor cells are administered concurrently with electrical and/or agent therapy, while in other approaches electrical and agent therapies are initiated subsequent to cell administration. In another approach, electrical and agent therapies are applied prior to cell administration. In one approach, cellular engraftment, cellular proliferation, cellular differentiation, cellular survival and/or cellular function, e.g., contractile function, of the donor cells in the recipient is further enhanced by the electrical therapy and/or agent administration. It is understood that different permutations of agent, cell and/or electrical therapy may be performed in varying embodiments.

Non-human animal models, e.g., rodent, lapine, canine or swine models, may be employed to determine agent, pacing and/or cellular parameters useful to inhibit or treat a particular indication or condition. See, e.g., Jain et al., *Circ.*, 103, 1920 (2001); Suzuki et al., *Circ.*, 104, 1-207 (2001); Pouleur et al., *Eur. J. Clin. Investig.*, 13, 331 (1983); Hammond, *J. Clin. Res.*, 92, 2644 (1993); Taylor et al., *Proc. Assoc. Am. Phys.*, 109, 245 (1997); and Roth et al., *J. Clin. Res.*, 91, 939 (1993)). In an animal model of MI, efficacious pacing and agent therapy may result in improvement in cardiac function, e.g., increased maximum exercise capacity, contractile performance, and propagation velocity, decreased deleterious remodeling, decreased post-scar expansion, decreased apoptosis, increased angiogenesis, and increased cell engraftment, survival, proliferation, and function, or a combination thereof. In ex vivo models, effects in hemodynamic performance, such as indicated by systolic and diastolic pressure-volume relations, can be used to determine the efficacy of a particular therapy.

Device

A system provides combined electrical and agent therapies to treat a heart having suffered myocardial infarction (MI). The electrical and agent therapies combine delivery of pacing pulses and delivery of one or more agents including biological agents, e.g., those encoded by DNA or isolated from cells, to reduce scar formation and/or promote myocardial tissue growth, e.g., replacement, in the infarct region. The agent modulates myocardial tissue growth, such as by promoting the localization of stem cells to the infarct region or modulating local fibrosis signaling. The pacing pulses enhance the environment for myocardial tissue growth, such as by altering wall stress and altering workload in a cardiac region including the infarct region. The combined electrical and agent therapies include temporally coordinated electrical therapy delivery and agent therapy delivery, and not necessarily simultaneous or concurrent deliveries of both therapies. The agent delivery and the pacing pulse delivery may be on a simultaneous, alternating, or any other coordinated basis designed for optimally modulating myocardial tissue growth. In the description of this system, the "agent" includes agents that are capable of directly or indirectly modulating myocardial tissue growth, including all such agents discussed in this document.

FIG. 1 is an illustration of an embodiment of a system 100 that delivers the combined electrical and agent therapies and portions of an environment in which system 100 is used. System 100 includes an implantable system 115 and an external system 145. Implantable system 115 includes an implantable cardiac rhythm management (CRM) device 110 and a lead system 108. The external system includes an external device 150, a network 160, and a remote device 170. Implantable CRM device 110 includes agent delivery capability. As shown in FIG. 1, implantable CRM device 110 is implanted in a body 102. Lead system 108 includes one or more pacing leads that provide electrical connections between a heart 105 and implantable CRM device 110. At least one lead of lead system 108 is an agent eluting lead that provides for fluid communication between implantable CRM device 110 and heart 105. A telemetry link 140 provides for bidirectional communication between implantable CRM device 110 and external device 150. Network 160 provides for bidirectional communication between external device 150 and remote device 170.

System 100 allows the delivery of the combined electrical and agent therapies to be controlled by any one of implantable CRM device 110, external device 150, and remote device 170. In one embodiment, implantable CRM device 110 controls the delivery of the combined electrical and agent therapies based on a detected predetermined signal or condition. External device 150 and/or remote device 170 control the delivery of the combined electrical and agent therapies upon receiving the external user command. In further embodiments, external device 150 and/or remote device 170 are capable of automated control of the delivery of the combined electrical and agent therapies by processing and analyzing signals and/or conditions detected by implantable CRM device 110.

Figure 2:
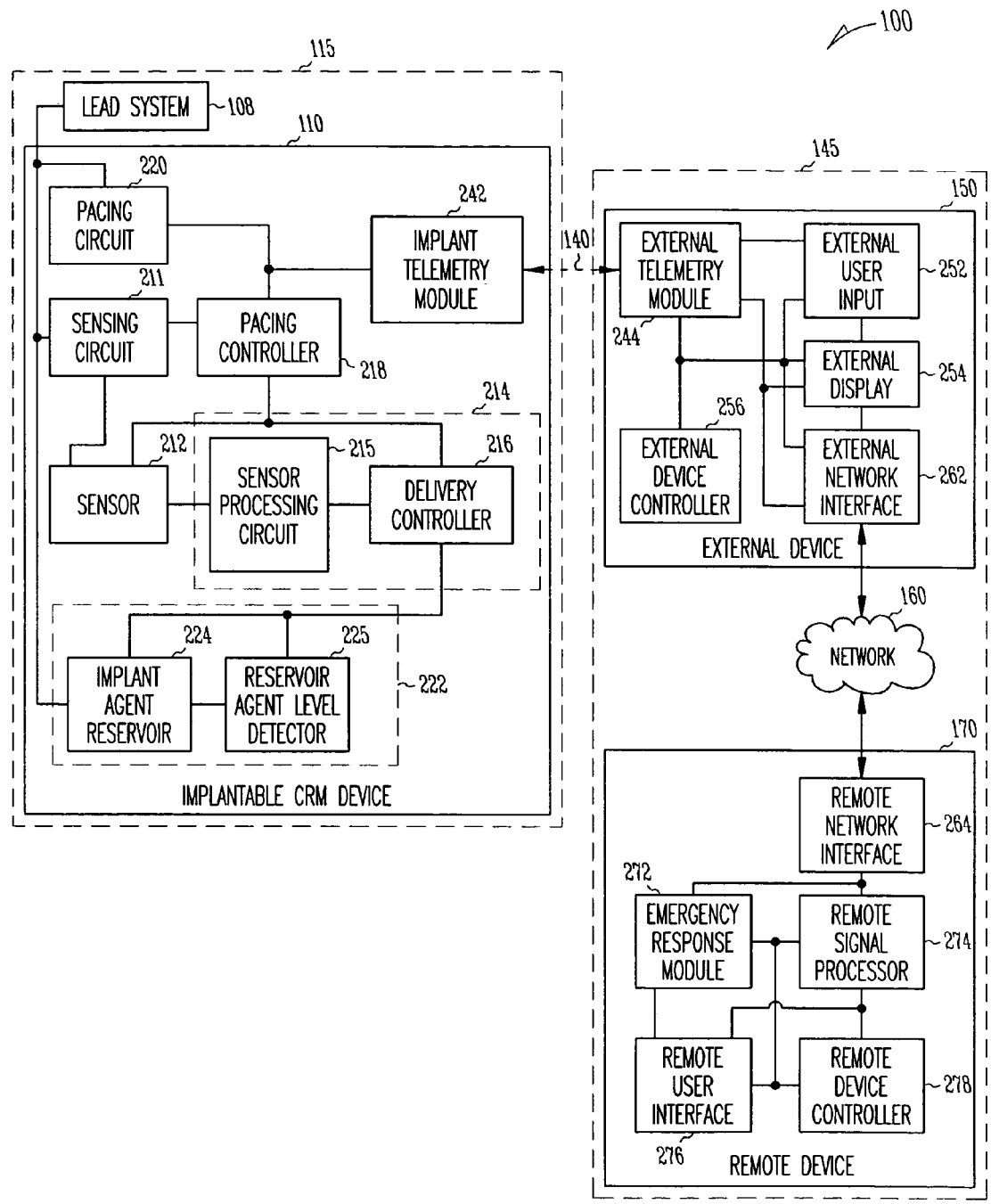
FIG. 2 is a block diagram showing one embodiment of the circuit of portions of the system such as shown in FIG. 1.

FIG. 2 is a block diagram showing one embodiment of the circuit of portions of the system 100.

Implantable CRM device 110 includes a sensing circuit 211, a sensor 212, an implantable processor 214, an implantable agent delivery device 222, a pacing controller 218, a pacing circuit 220, and an implant telemetry module 242. Sensing circuit 211 senses one or more intracardiac electrograms through one or more pacing leads of lead system 108. Sensor 212 senses one or more signals used to control the delivery of the combined electrical and agent therapies. Implantable processor 214 includes a sensor processing circuit 215 and an agent delivery controller 216. Sensor processing circuit 215 processes the signal sensed by sensor 212 to produce one or more parameters indicative of a need for starting, stopping, or adjusting the agent delivery and/or the pacing pulse delivery. Agent delivery controller 216 produces an agent delivery signal based on the parameter from sensor processing circuit 215 and the external user command. Implantable agent delivery device 222 includes an implant agent reservoir 224 and a reservoir agent level detector 225. Implant agent reservoir 224 contains the one or more agents to be delivered. Reservoir agent level detector 225 monitors the amount of the one or more agents remaining in implant agent reservoir 224 and produces an agent-level-low alert signal when the amount of the one or more agents is below a predetermined level. The agent-level-low alert signal is transmitted to remote device 170 to inform the physician or other caregiver. In the embodiment shown in FIG. 2, implantable agent delivery device 222 is a functional module housed within implantable CRM device 110. Pacing controller 218 includes a pacing algorithm execution module to control the delivery of pacing pulses by executing a pacing algorithm designed for enhancing one or more effects of the one or more agents in the modulation of myocardial tissue growth. In one specific embodiment, the pacing algorithm execution module executes a remodeling control therapy (RCT) pacing algorithm. The RCT reduces the degree of post MI remodeling, for example, by redistributing the loading or stress on the ventricular walls. An example of post MI RCT is discussed in U.S. Patent Application Publication No. 2003/0105493 A1, "METHOD AND APPARATUS FOR MINIMIZING POST-INFARCT VENTRICULAR REMODELING," assigned to Cardiac Pacemakers, Inc., which is hereby incorporated by reference in their entirety. In another specific embodiment, the pacing algorithm execution module executes a cardiac resynchronization therapy (CRT) pacing algorithm. The CRT provides for an approximately optimal hemodynamic performance. In one embodiment, a CRT pacing algorithm is executed with one or more pacing parameters approximately optimized to maximize a measure of hemodynamic performance. Examples of determining such pacing parameters are discussed in U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," and U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," both filed on Dec. 9, 2002, assigned to Cardiac Pacemakers, Inc., which are hereby incorporated by reference in their entirety. In a further specific embodiment, the pacing algorithm execution module executes a dynamic pacing algorithm that dynamically adjusts pacing parameters based on a patient's changing needs and conditions. One example of such a dynamic pacing algorithm is discussed U.S. patent application Ser. No. 10/744,900, "DYNAMIC DEVICE THERAPY CONTROL FOR TREATING POST MYOCARDIAL INFARCTION PATIENTS," filed on Dec. 22, 2003, which is hereby incorporated by reference in its entirety. Pacing circuit 220 includes one or more pulse output channels to deliver the pacing pulses to one or more sites in heart 105 through lead system 408, with the timing and other parameters of the pacing pulses controlled by pacing controller 218.

In one embodiment, sensor processing circuit 215 processes the signal sensed by sensor 212 before the signal is used by agent delivery controller 216 and pacing controller 218 to determine whether to start, stop, or adjust the combined electrical and agent therapies. The one or more parameters produced by sensor processing circuit 215 include parameters measured and/or derived from the sensed signal. In one embodiment, sensor processing circuit 215 includes an event detector to detect one or more predetermined events indicative of a need to start, stop, or adjust the combined electrical and agent therapies. The one or more parameters produced by sensor processing circuit 215 include parameters indicative of the detection of the event and/or measured parameters associated with the detected event. In one specific embodiment, the event includes an abnormal condition. In one embodiment, sensor 212 includes a plurality of sensors to sense multiple signals used by agent delivery controller 216 and pacing controller 218 to determine whether to start, stop, or adjust the combined electrical and agent therapies. Each of the multiple signals may be used by agent delivery controller 216 to control the agent therapy, by pacing controller 218 to control the electrical therapy, or by both controllers to control both the agent and electrical therapies.

In one embodiment, sensor 212 includes at least one electrogram sensing channel of sensing circuit 211, and sensor processing circuit 215 includes an event detector to detect an arrhythmia. In one embodiment, the event detector of sensor processing circuit 215 detects the arrhythmia by detecting heart rate and comparing the heart rate to one or more threshold rates. A bradycardia condition is detected when the heart rate falls below a bradycardia threshold. A tachycardia condition is detected when the heart rate exceeds a tachycardia threshold. In a further embodiment, the event detector of sensor processing circuit 215 detects the arrhythmia also by detecting morphological features of the electrogram to one or more predetermined templates. In one specific embodiment, the event detector of sensor processing circuit 215 includes an atrial fibrillation detector. In one specific embodiment, the event detector of sensor processing circuit 215 includes a ventricular fibrillation detector. In one embodiment, the electrical therapy includes cardioversion/defibrillation shock delivery in addition to the pacing pulse delivery, and implantable CRM device further includes a defibrillation controller and a defibrillation circuit.

In one embodiment, sensor 212 senses a physiological signal indicative of ischemia, and sensor processing circuit 215 includes an ischemia detector. In one specific embodiment, sensor 212 senses an electrogram and the event detector of sensor processing circuit 215 runs an automatic ischemia detection algorithm to detect an ischemic condition from the electrogram. One specific example of an electrogram-based ischemia detector is discussed in Zhu et al., U.S. patent application Ser. No. 09/962,852, entitled "EVOKED RESPONSE SENSING FOR ISCHEMIA DETECTION," filed on Sep. 25, 2001, assigned to Cardiac Pacemakers, Inc., which is incorporated herein by reference in its entirety. In another embodiment, sensor 212 includes an electrical impedance based sensor using a low carrier frequency (e.g. 100 Hz), and the ischemia detector runs an automatic ischemia detection algorithm to detect an ischemic condition from the electrical impedance signal. Tissue electrical impedance has been shown to increase significantly during ischemia, as discussed in Min, et al. *International Journal of Bioelectromagnetism*, 5(1): 53-56 (2003). Sensor 212 senses low frequency electrical impedance signal between electrodes interposed in the heart. The event ischemia detector detects the ischemia as abrupt changes in impedance (such as abrupt increases in value). In another specific embodiment, sensor 212 includes a local heart motion based sensor utilizing an accelerometer located within a lead body positioned on or in the heart, and the ischemia detector runs an automatic ischemia detection algorithm to detect an ischemic condition from the acceleration signal. The ischemia detector detects ischemia as an abrupt decrease in the amplitude of local cardiac accelerations.

In one embodiment, sensor 212 includes a metabolic sensor that senses a metabolic signal indicative of a cardiac metabolic level (rate of metabolism of cardiac cells). Examples of the metabolic sensor include a pH sensor, an oxygen pressure ($PO_2$) sensor, a carbon dioxide pressure ($PCO_2$) sensor, a glucose sensor, a creatine sensor, a C-creative protein sensor, a creatine kinase sensor, a creatine kinase-MB sensor, and any combination of such sensors. In one further embodiment, sensor processing circuit 215 includes an event detector to determine the cardiac metabolic level from the metabolic signal and compares the cardiac metabolic level to one or more predetermined thresholds defining a normal cardiac metabolic range. An abnormal condition, which may be indicative of an ischemic condition, is detected when the cardiac metabolic level is outside of the normal cardiac metabolic range.

In one embodiment, sensor 212 includes an implantable impedance sensor to measure pulmonary impedance, or impedance of a portion of the thoracic cavity. In a further embodiment, sensor processing circuit 215 includes an event detector to detect an abnormal condition when the impedance is out of its normal range. For example, pulmonary edema, i.e., fluid retention in the lungs resulting from the decreased cardiac output, increases the pulmonary or thoracic impedance. Thus, the abnormal condition may be indicative of decompensated heart failure. In one specific embodiment, the event detector produces the alert signal when the pulmonary or thoracic impedance exceeds a predetermined threshold impedance. In one embodiment, the impedance sensor is a respiratory sensor that senses the patient's minute ventilation. An example of an impedance sensor sensing minute ventilation is discussed in U.S. Pat. No. 6,459,929, "IMPLANTABLE CARDIAC RHYTHM MANAGEMENT DEVICE FOR ASSESSING STATUS OF CHF PATIENTS," assigned to Cardiac Pacemakers, Inc., which is incorporated herein by reference in its entirety.

In one embodiment, sensor 212 includes a pressure sensor. In a further embodiment, sensor processing circuit 215 includes an event detector to detect an abnormal condition when a pressure is outside of its normal range. The abnormal condition may be indicative of arrhythmias and/or heart failure that cause pressures in various portions of the cardiovascular system to deviate from their normal ranges. Such an abnormal condition demands application or adjustment of at least the electrical therapy. In one specific embodiment, sensor processing circuit 215 includes a systolic dysfunction detector to detect an abnormal condition related to pressure during the systolic phase of a cardiac cycle. In another specific embodiment, sensor processing circuit 215 includes a diastolic dysfunction detector to detect an abnormal condition related to pressure during the diastolic phase of a cardiac cycle. Examples of the pressure sensor include but are not limited to a left atrial (LA) pressure sensor, a left ventricular (LV) pressure sensor, an artery pressure sensor, and a pulmonary artery pressure sensor. Pulmonary edema results in elevated LA and pulmonary arterial pressures. A deteriorated LV results in decreased LV and arterial pressures. In various embodiments, the event detector of sensor processing circuit 215 detects an abnormal condition when the LA pressure exceeds a predetermined threshold LA pressure level, when the pulmonary arterial pressure exceeds a predetermined threshold pulmonary arterial pressure level, when the LV pressure falls below a predetermined threshold LV pressure level, and/or when the arterial pressure falls below a predetermined threshold LV pressure level. In other embodiments, sensor processing circuit 215 derives a parameter from one of these pressures, such as a rate of change of a pressure, and produces a signal when the parameter deviates from its normal range. In one embodiment, the LV pressure sensor senses the LV pressure indirectly, by sensing a signal having known or predictable relationships with the LV pressure during all or a portion of the cardiac cycle. Examples of such a signal include but are not limited to an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety.

In one embodiment, sensor 212 includes a cardiac output or stroke volume sensor. Examples of stroke volume sensing are discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," and U.S. Pat. No. 5,284,136, "DUAL INDIFFERENT ELECTRODE PACEMAKER," both assigned to Cardiac Pacemakers, Inc., which are incorporated herein by reference in their entirety. In a further embodiment, sensor processing circuit 215 includes an event detector to detect an abnormal condition when the stroke volume falls below a predetermined threshold level. The abnormal condition may be indicative of decompensated heart failure.

In one embodiment, sensor 212 includes a neural activity sensor to detect activities of the sympathetic nerve and/or the parasympathetic nerve. A significant decrease in cardiac output immediately stimulates sympathetic activities, as the autonomic nervous system attempts to compensate for deteriorated cardiac function. In one specific embodiment, the neural activity sensor includes a neurohormone sensor to sense a hormone level of the sympathetic nerve and/or the parasympathetic nerve. In a further embodiment, sensor processing circuit 215 includes an event detector to detect an abnormal condition when the hormone level exceeds a predetermined threshold level. In another specific embodiment, the neural activity sensor includes an action potential recorder to sense the electrical activities in the sympathetic nerve and/or the parasympathetic nerve. In a further embodiment, sensor processing circuit 215 includes an event detector to detect the abnormal condition when the frequency of the electrical activities in the sympathetic nerve exceeds a predetermined threshold level. Examples of direct and indirect neural activity sensing are discussed in U.S. Pat. No. 5,042,497, "ARRHYTHMIA PREDICTION AND PREVENTION FOR IMPLANTED DEVICES," assigned to Cardiac Pacemakers, Inc., which is hereby incorporated by reference in its entirety. The abnormal condition may be indicative of heart failure.

In one embodiment, sensor 212 includes a heart rate variability detector. An example of detecting the heart rate variability is discussed in U.S. Pat. No. 5,603,331, "DATA LOGGING SYSTEM FOR IMPLANTABLE CARDIAC DEVICE," assigned to Cardiac Pacemakers, Inc., which is incorporated herein by reference in their entirety. In a further embodiment, sensor processing circuit 215 includes an event detector to detect the abnormal condition when the heart rate variability falls below a predetermined threshold level. The abnormal condition may be indicative of decompensated heart failure.

In one embodiment, sensor 212 includes a renal function sensor. Decompensated heart failure results in peripheral edema primarily because of fluid retention of the kidneys that follows the reduction in cardiac output. The fluid retention is associated with reduced renal output, decreased glomerular filtration, and formation of angiotensin. Thus, in one specific embodiment, the renal function sensor includes a renal output sensor to sense a signal indicative of the renal output. In a further embodiment, sensor processing circuit 215 includes an event detector to detect an abnormal condition when the sensed renal output falls below a predetermined threshold. In another specific embodiment, the renal function sensor includes a filtration rate sensor to sense a signal indicative of the glomerular filtration rate. In a further embodiment, sensor processing circuit 215 includes an event detector to detect an abnormal condition when the sensed glomerular filtration rate falls below a predetermined threshold. In yet another specific embodiment, the renal function sensor includes a chemical sensor to sense a signal indicative of angiotensin II levels. In a further embodiment, sensor processing circuit 215 includes an event detector to detect an abnormal condition when the sensed angiotensin II levels exceed a predetermined threshold level. Such abnormal conditions may be indicative of decompensated heart failure.

In one embodiment, sensor 212 includes an acoustic sensor being a heart sound sensor and/or a respiratory sound sensor. Arrhythmias and/or heart failure cause abnormal cardiac and pulmonary activity patterns and hence, deviation of heart sounds and respiratory sounds from their normal ranges of pattern and/or amplitude. In a further embodiment, sensor processing circuit 215 includes an event detector to detect an abnormal condition when the heart sound or respiratory sound is out of its normal range. For example, detection of the third heard sound (S3) is known to indicate heart failure. In one specific embodiment, sensor processing circuit 215 includes an event detector to detect an abnormal condition when the S3 amplitude or activity exceeds a predetermined threshold level.

In one embodiment, sensor 212 includes a displacement sensor to sense a signal indicative of a strain of myocardial tissue. After MI, myocardial tissue in the infarct region becomes less elastic due to the scar formation process. By modulating myocardial tissue growth, the agent therapy reduces the scar formation and/or promotes myocardial tissue replacement, thus reducing the loss of the elasticity and/or restores it. Therefore, the strain of myocardial tissue is indicative of a need for the therapy as well as the results of the therapy. In a further embodiment, sensor processing circuit 215 includes an event detector to detect an abnormal condition when the sensed strain of myocardial tissue falls below a predetermined threshold. The abnormal condition is indicative of a degree of myocardial tissue scar formation.

In one embodiment, sensor 212 includes a remodeling sensor to sense a signal indicative a degree of myocardial remodeling. In one specific embodiment, the remodeling sensor includes two or more piezoelectric crystals incorporated in one or more leads of lead system 108 to sense a size of an injured myocardial region such as an infarct region. The size of the injured myocardial region is estimated based on spatial information sensed by the crystals and averaged over a predetermined period of time. In one embodiment, a substantial degree of change in the size of the injured region indicates a need to start, stop, or adjust the combined electrical and agent therapies. In another specific embodiment, sensor 212 includes a hypertrophic sensor to sense a signal indicative of a degree of myocardial hypertrophy, which indicates the progress of the remodeling process. In another specific embodiment, sensor 212 includes a chemical sensor to sense the change in expression or concentration of Endothelin-1 (ET-1), BNP, or p38MAPK, which are known to change during hypertrophy response. In a further embodiment, sensor processing circuit 215 includes an event detector to detect an abnormal condition when the degree of myocardial remodeling exceeds a predetermined threshold. The degree of myocardial remodeling is represented by one or more of the degree of change in the size of the injured region, the degree of myocardial hypertrophy, and the degree of the change in expression or concentration of Endothelin-1 (ET-1), BNP, or p38MAPK.

In one embodiment, sensor 212 includes a thermal sensor to sense a signal indicative of a perfusion of thermal energy in myocardial tissue. In one specific embodiment, the thermal sensor includes a thermal energy source to heat or cool at least a portion of the myocardial tissue including the infract region, a temperature sensor to sense the temperature in the infarct region, and a perfusion calculator to calculate the rate of change in the temperature in the infarct region. The ability of myocardial tissue to perfuse thermal energy reduces with the post MI scar formation process. Therefore, the rate of change in the temperature, as a measure of thermal perfusion, is indicative of a need for the therapy as well as the results of the therapy. In a further embodiment, sensor processing circuit 215 includes an event detector to detect an abnormal condition when the rate of change in the temperature falls below a predetermined threshold. This abnormal condition is indicative of a degree of myocardial tissue scar formation.

Embodiments of sensor 212 and the event detector of sensor processing circuit 215 are discussed in this document by way of example, but not by way of limitation. In various embodiment, sensor 212 and the event detector of sensor processing circuit 215 may include combinations of various sensors and detectors discussed above. Other methods and sensors for directly or indirectly detecting an abnormal condition demanding the start, stop, or adjustment of the combined electrical and agent therapies are also usable by system 100.

Implantable CRM device 110 includes a hermetically sealed metal can to house at least portion of the electronics of the device. In one embodiment, sensor 212 resides within the metal can. In another embodiment, sensor 212 is outside of the metal can. In one embodiment, sensor 212 is incorporated into lead system 108

Lead system 108 includes one or more pacing leads allowing sensing of electrical signals from heart 105 and delivery of pacing pulses to heart 105. In one embodiment, lead system 108 includes one or more transvenous leads each having at least one sensing-pacing electrode disposed within heart 105. In one embodiment, lead system 108 includes one or more epicardial leads each having at least one sensing-pacing electrode disposed on the epicardial wall of heart 105. Lead system 108 includes at least one agent eluting lead connected to implant agent reservoir 224. In one embodiment, the agent eluting lead includes a fluid passageway having one opening at one end of the lead connected to implant agent reservoir 224 and another opening connected to an agent eluting electrode at or near the other end of the lead that is to be disposed in or about heart 105. The fluid passageway allows fluid communication between implant agent reservoir 224 and the location to which the agent is released. Thus, lead system 108 allows sensing of electrical signals from heart 105 and delivery of pacing pulses to heart 105, as well as delivering a fluid agent to heart 105. In one embodiment, lead system 108 includes an endocardial lead including at least one agent eluting electrode configured to be disposed within one of a coronary sinus and a portion of a great cardiac vein adjacent to the left ventricle of heart 105. In another embodiment, lead system 408 includes an epicardial lead including at least one agent eluting electrode configured to be attached to a portion of an epicardial wall of heart 105. In one embodiment, sensor 212 is built-in or attached to a lead of lead system 108, such that when the lead is implanted, sensor 212 is in a blood pool.

External device 150 includes an external user input 252, an external display 254, an external device controller 256, an external telemetry module 244, and an external network interface 262. External user input 252 receives the external user command controlling the combined electrical and agent therapies from the physician or other caregiver. In a further embodiment, it also receives other commands or instructions to control the operation implantable CRM device 110 including implantable agent delivery device 222. External device 150 transmits the external user command to implantable CRM device 110, resulting in a production of the agent delivery control signal by agent delivery controller 213. In one embodiment, the external user command controlling the combined electrical and agent therapies is sent from remote device 170. External device 150 relays the external user command to implantable CRM device 110, resulting in a production of an agent delivery signal by agent delivery controller 213. External telemetry module 244 provides for a telemetry interface allowing external device 150 to communicate with implantable CRM device 110 via telemetry link 140. External network interface 262 provides for a network interface allowing external device 150 to communicate with remote device 170 via network 160.

Telemetry link 140 is a wireless bidirectional data transmission link supported by implant telemetry module 242 and external telemetry module 244. In one embodiment, telemetry link 140 is an inductive couple formed when two coils—one connected to implant telemetry module 242 and the other connected to external telemetry module 244—are placed near each other. In another embodiment, telemetry link 140 is a far-field radio-frequency telemetry link allowing implantable CRM device 110 and external device 252 to communicate over a telemetry range that is at least ten feet.

Remote device 170 includes an emergency response module 272, a remote signal processor 274, a remote user interface 276, a remote device controller 278, and a remote network interface 264. By executing one or more predetermined algorithms, remote signal processor 274 processes signals transmitted from external device 150 and signals transmitted from implantable CRM device 110. Emergency response module 272 contacts the physician or other caregiver or other emergency response personnel in response to an emergency situation as detected by one of implantable CRM device 110, external device 150, and remote device 170. In one embodiment, external device 150 transmits the external user command to remote device 170 as a request for further medical attention through emergency response module 272. In another embodiment, remote signal processor 274 analyzes signals acquired by implantable CRM device 110 and transmitted to remote device 170, such as the one or more electrograms sensed by sensing circuit 211 and one or more signals sensed by sensor 212, to determine the need for starting, stopping, or adjusting the combined electrical and agent therapies. Remote user interface 276 includes a remote user input to allow the physician or other caregiver to enter the external user command from a remote location. In one embodiment, implantable CRM device 110 transmits the agent-level-low alert signal to remote device 170 as a request a refill through remote user interface 276. Remote device controller 278 controls the overall operation of remote device 170. In one embodiment, remote device controller 278 generates commands controlling implantable CRM device 110 and/or external device 150 based on the received signals and the external user command. In a further embodiment, remote device controller 278 generates commands controlling the settings of sensor 212, implantable processor 214, and implantable agent delivery device 222. In one embodiment, remote device controller 278 executes an automatic algorithm to control the combined electrical and agent therapies, such as when the physician or other caregiver is not immediately available. Remote network interface 264 provides for an interface allowing communication between remote device 170 and external device 150 via network 160.

Network 160 provides long distance bidirectional communication between external device 150 and remote device 170. It allows management of multiple implantable systems, such as multiple units of implantable system 115 implantable in multiple patients, from a central facility at a remote location. In one embodiment, this allows prompt response by a physician or other caregiver at the central facility as demanded by the condition of a patient. In one embodiment, network 160 is based on a wireless communications system. In another embodiment, network 160 is based on a wired communications system. In one embodiment, network 160 utilizes portions of a standard communications system such as the Internet, a telephone system, or a radio frequency telemetry system.

Figure 3:
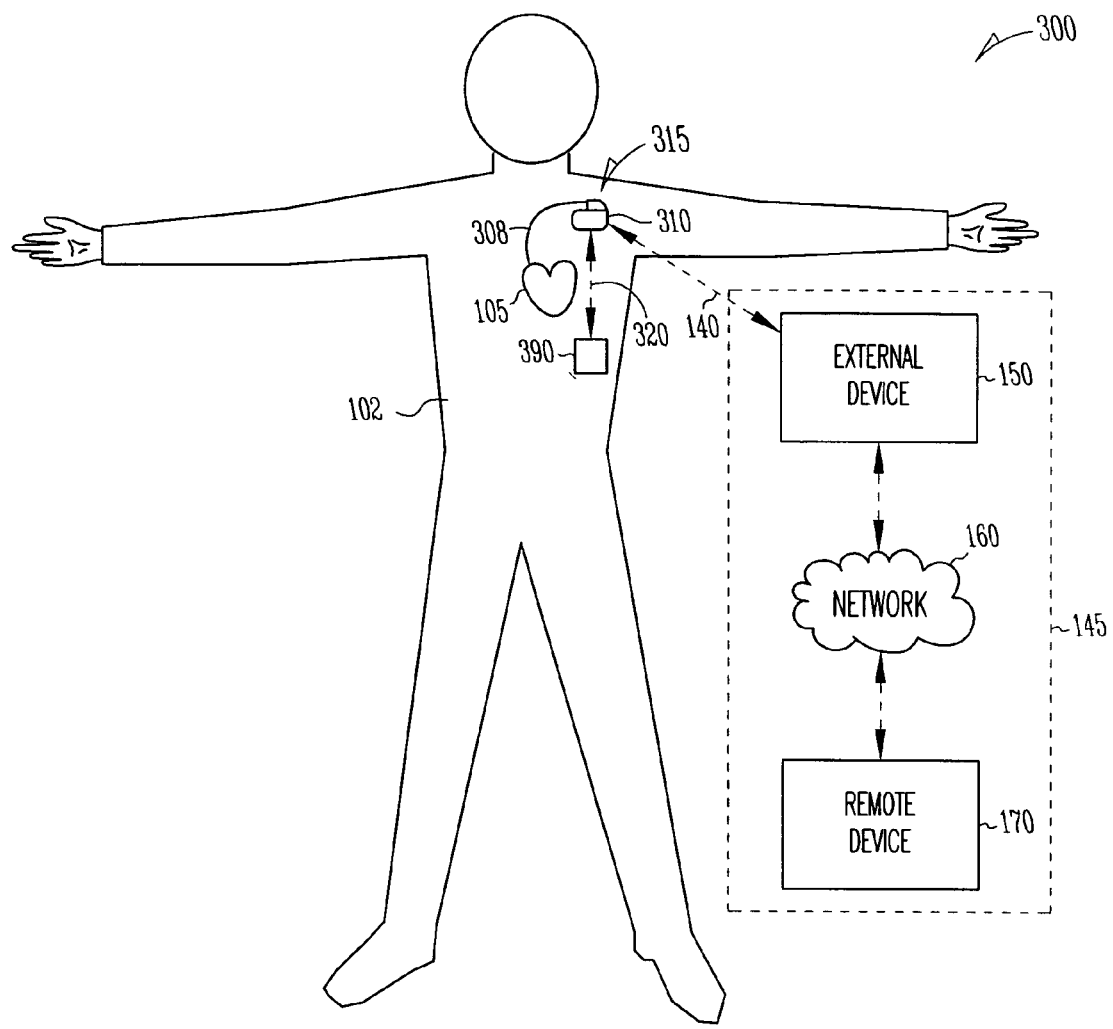
FIG. 3 is an illustration of an embodiment of another system delivering combined electrical and agent therapies a heart and portions of an environment in which it is used.

FIG. 3 is an illustration of an embodiment of another system 300 delivering the combined electrical and agent therapies to a heart and portions of an environment in which it is used. System 300 includes an implantable CRM device 310, an implantable agent delivery device 390, and a communication link 320 between the two devices. Lead system 308 provides for one or more electrical connections between implantable CRM device 310 and heart 105 through which the electrical therapy is delivered. Identical numerals appearing in both FIGS. 1 and 3 indicate corresponding system components included in systems 100 and 300 that are substantially identical. In one embodiment, system 300 differs from system 100 by having the implantable agent delivery device physically separate from the implantable CRM device.

System 300 allows the delivery of the combined electrical and agent therapies to be controlled by any one of implantable CRM device 310, external device 150, and remote device 170. In one embodiment, implantable CRM device 310 controls the delivery of the combined electrical and agent therapies based on a detected predetermined signal or condition. External device 150 and/or remote device 170 control the delivery of the combined electrical and agent therapies upon receiving the external user command. In further embodiments, external device 150 and/or remote device 170 are capable of automated control of the delivery of the combined electrical and agent therapies by processing and analyzing signals and/or condition detected by implantable CRM device 310.

Figure 4:
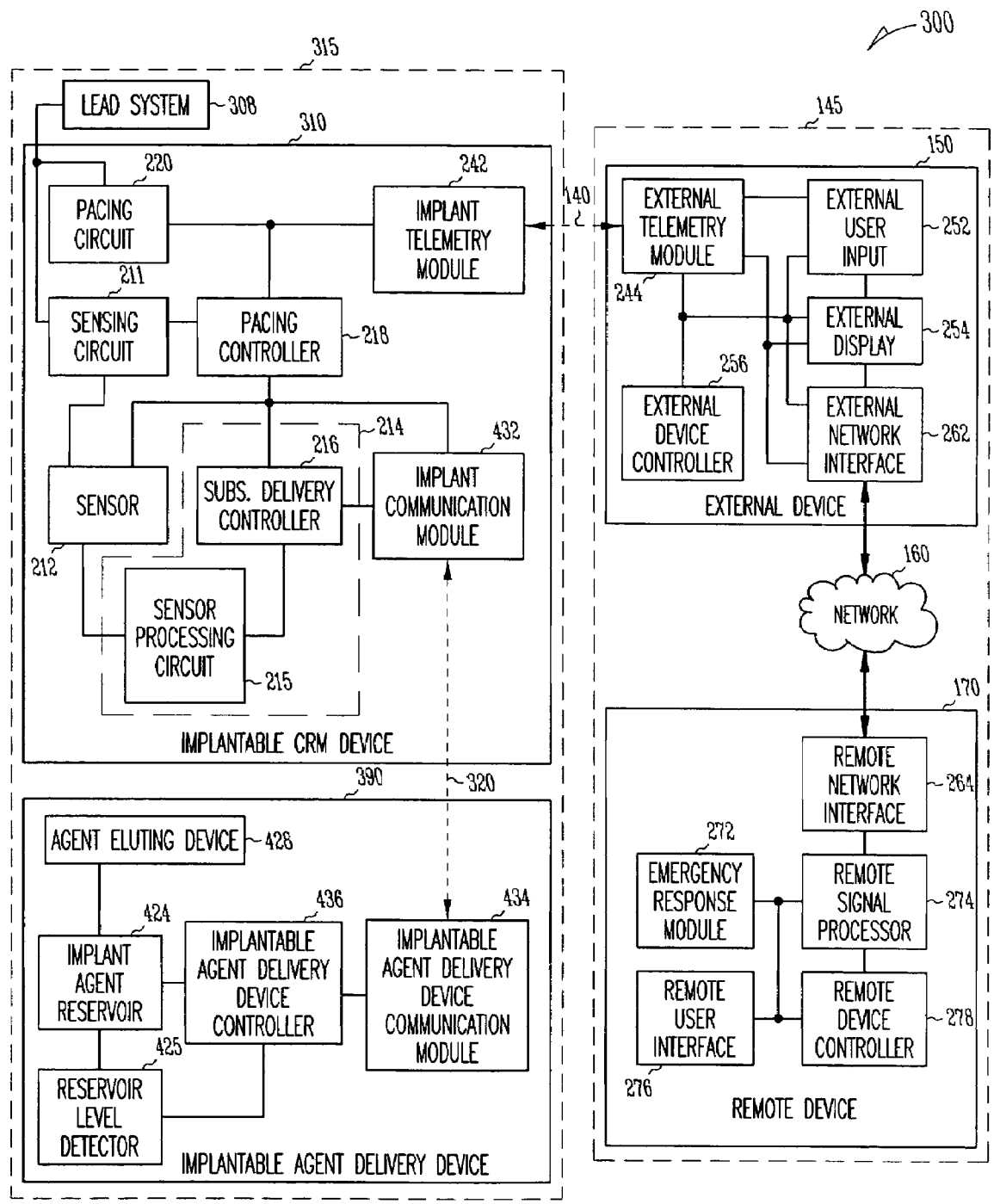
FIG. 4 is a block diagram showing one embodiment of the circuit of portions of the system such as shown in FIG. 3.

FIG. 4 is a block diagram showing one embodiment of the circuit of portions of system 300. Identical numerals appearing in both FIGS. 2 and 4 indicate corresponding system components included in systems 100 and 300 that are substantially identical. In general, implantable CRM device 310 retains, among other components, sensor 212 and implantable processor 214 of implantable CRM device 110, where implantable processor 214 includes sensor processing circuit 215 and agent delivery controller 216. Implantable agent delivery device 222 of implantable CRM device 110 is replaced by a separate implantable device, that is, implantable agent delivery device 390.

Implantable agent delivery device 390 includes implant agent reservoir 424, reservoir agent level detector 425, agent eluting device 428, implantable agent delivery device controller 436, and implantable agent delivery device communication module 434. Implant agent reservoir 424 contains the agent to be delivered. Reservoir agent level detector 425 monitors the amount of the agent remaining in implant agent reservoir 424 and produces the agent-level-low alert signal when the amount of the agent is below a predetermined level. Implantable agent delivery device controller 436 controls the overall operation of implantable agent delivery device 390. Implantable agent delivery device communication module 434 and an implant communication module 432 of implantable CRM device 310 support communication link 320. In one embodiment, communication link 320 is a telemetry link. In another embodiment, implantable CRM device 310 and implantable agent delivery device 390 each transmit electrical signals into tissue of body 102, to be received by the other device through electrical conduction using tissue as the medium. One specific example of such a communication link is discussed in U.S. Pat. No. 6,689,117, "DRUG DELIVERY SYSTEM FOR IMPLANTABLE MEDICAL DEVICE," assigned to Cardiac Pacemakers, Inc., which is incorporated herein by reference in its entirety.

Agent eluting device 428 is connected to implant agent reservoir 424 to allow fluid communication between implant agent reservoir 424 and the body location to which the agent is released. In one embodiment, agent eluting device 428 includes at least one electrode connected to implant agent reservoir 224. In one specific embodiment, the electrode is disposed in blood to allow the agent to be released to the blood. In another specific embodiment, the electrode is disposed in tissue to allow the agent to be diffused into tissue. In one embodiment, agent eluting device 422 allows electrically controlled agent delivery by, for example, iontophoresis, electroporation, electrorepulsion, or electro-osmosis.

In one embodiment, implantable agent delivery device 390 is constructed as an agent eluting epicardial patch for attachment onto the epicardial wall of heart 105. In one embodiment implantable agent delivery device 390 is incorporated into another implantable device (other than implantable CRM device 310), such as a coronary stent or other devices implanted in or about the heart or the vascular system.

Figure 5:
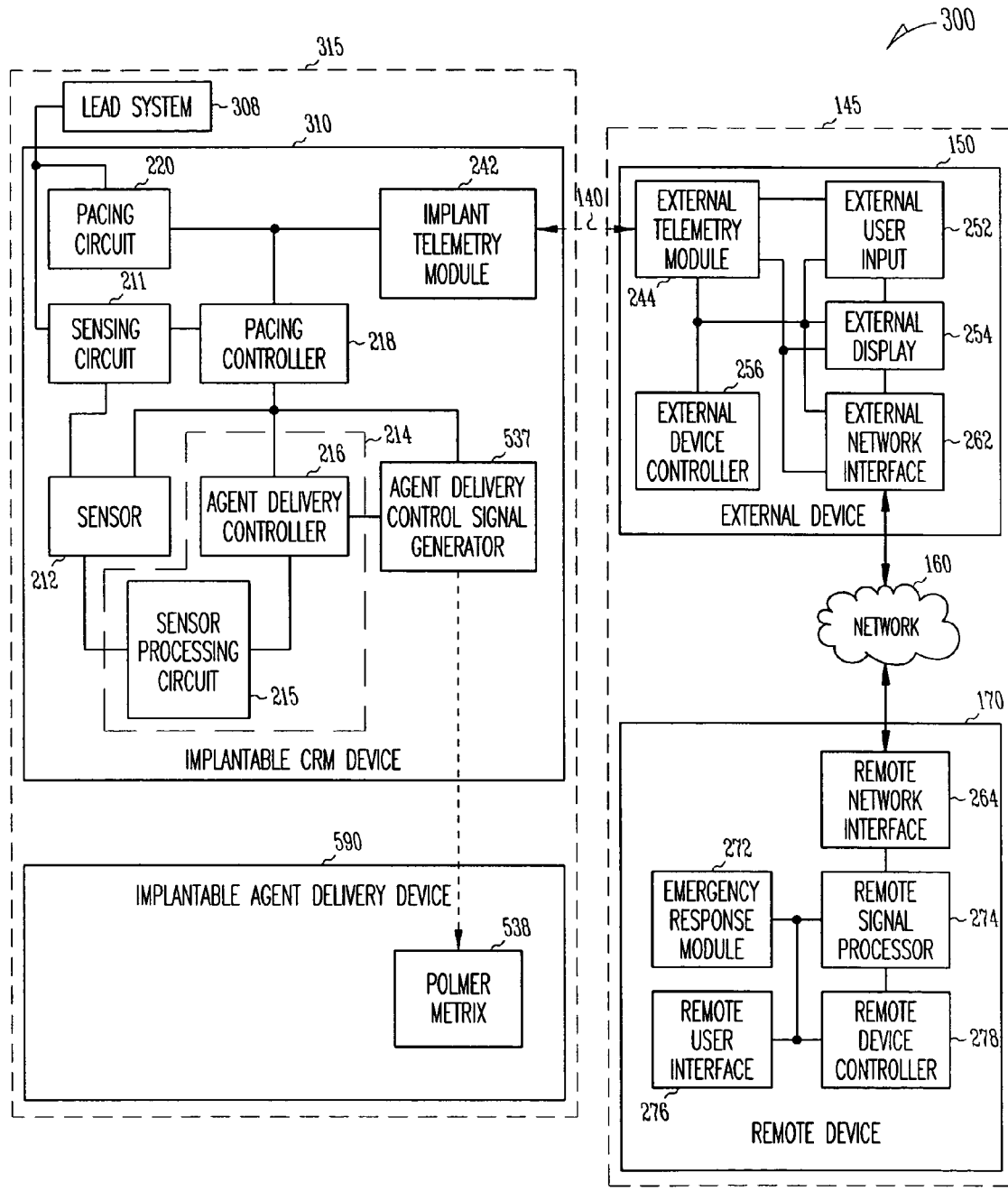
FIG. 5 is a block diagram showing another embodiment of the circuit of portions of the system such as shown in FIG. 3.

FIG. 5 is a block diagram showing another embodiment of the circuit of portions of the system such as shown in FIG. 3. Identical numerals appearing in FIGS. 4 and 5 indicate corresponding system components included both embodiments that are substantially identical. In this embodiment, the implantable agent delivery device of system 300 is an implantable agent delivery device 590, which includes a polymer matrix 538 providing for electrically-controlled agent delivery by iontophoresis. Polymer matrix 538 includes a porous polymer that is sensitive to an electric field applied on it. The agent is embedded in the polymer. Implantable CRM device 310 includes an agent delivery control signal generator 537 that generates a signal causing an electrical field to be applied on polymer matrix 538 according to the agent delivery signal from agent delivery controller 216. In one embodiment, agent delivery control signal generator 537 creates an electric field in tissue surrounding implantable agent delivery device 590 through electrodes placed in the vicinity of implantable agent delivery device 590. In another embodiment, agent delivery control signal generator 537 is electrically connected to implantable agent delivery device 590 via a wired connection, such that the electrical field is created upon polymer matrix 538 by applying a voltage across it. A change in the electric field changes the size of the pores in the polymer and/or the binding affinity of the polymer, resulting in controlled release of the agent.

In one embodiment, implantable agent delivery device 590 is constructed as an agent eluting epicardial patch for attachment onto the epicardial wall of heart 105. In one specific embodiment, electrical stimuli (e.g., pacing pulses) cause the agent to release from polymer matrix 538, embedded in the agent eluting epicardial patch, to the myocardial tissue, in response to the changing electric field created by the electrical stimuli. In one embodiment, implantable agent delivery device 590 is incorporated into another implantable device (other than implantable CRM device 310), such as a coronary stent, an intracardiac or epicardial pacing lead of lead system 308, or other devices implanted in or about the heart or the vascular system. In one specific example, an agent eluting coronary stent is placed near a pacing electrode of lead system 308. The electrical stimuli (e.g., pacing pulses) cause the agent to release from polymer matrix 538, in response to the changing electric field created by the electrical stimuli.

Figure 6:
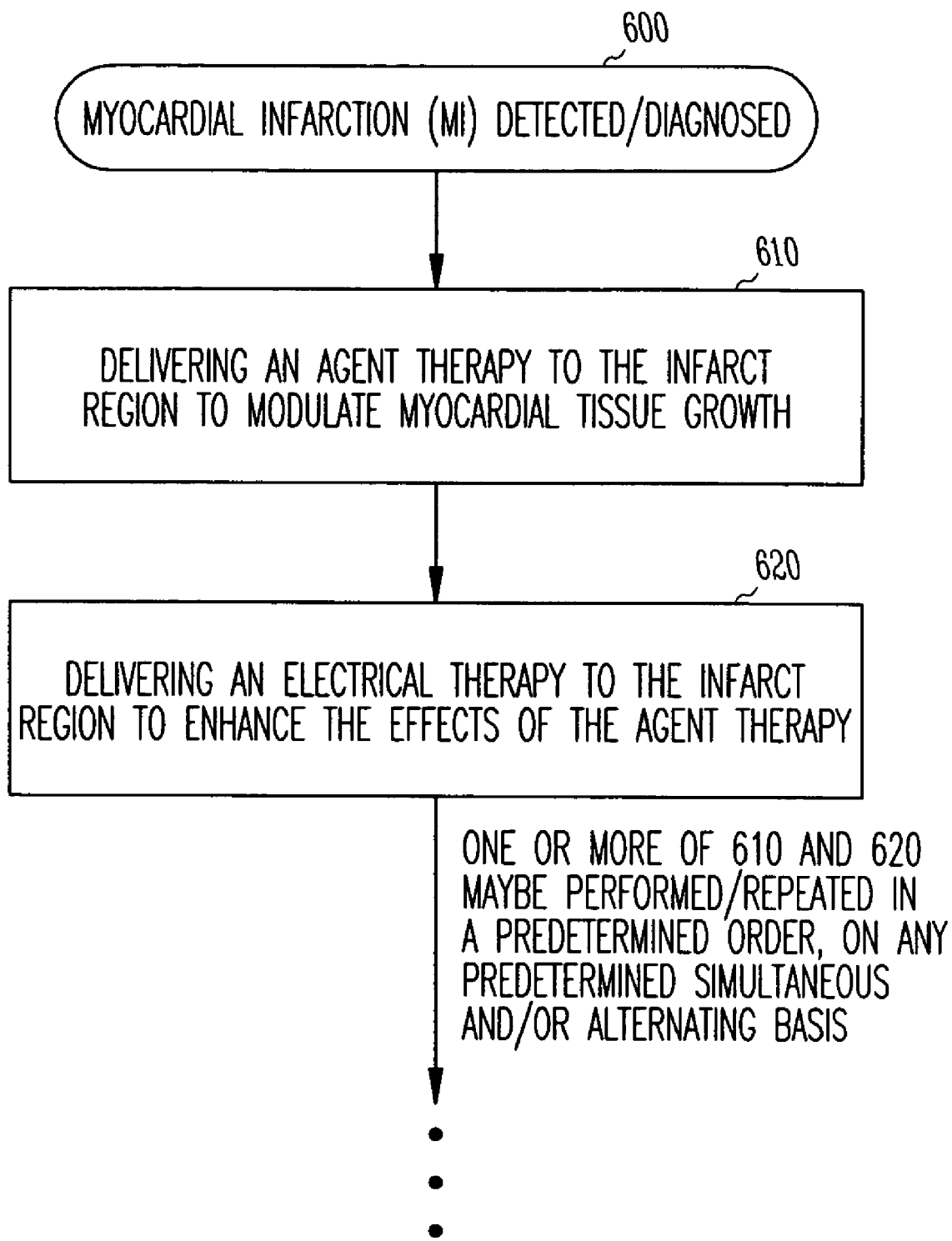
FIG. 6 is a flow chart illustrating a method for delivering combined electrical and agent therapies.

FIG. 6 is a flow chart illustrating a method for delivering the combined electrical and agent therapies. In response to a detection or diagnosis of MI at 600, an agent therapy is delivered to the infarct region(s) of the myocardium to modulate myocardial tissue growth at 610, and an electrical therapy is delivered to the infarct region to enhance the effects of the agent therapy at 620. The flow chart of FIG. 6 is not intended to limit or suggest any particular order by which the agent therapy and the electrical therapy are delivered. Steps 610 and 620 may be performed, and either of both of the steps may be repeated, in any predetermined order or sequence. In one embodiment, the agent therapy and the electrical therapy are temporally coordinated based on a patient's overall cardiac condition, such as degree of post MI remodeling, degree of scar formation, and hemodynamic performance. Because such cardiac conditions change over time, the agent therapy and the electrical therapy are adjusted on an ongoing basis. The adjustment may include temporal coordination of the agent therapy and the electrical therapy, adjustment of pacing algorithm and/or parameters, and/or adjustment of amount and content of the agent.

In one embodiment, the agent is delivered to a cardiac region including at least portions of the infarct region in an amount effective to modulate myocardial tissue growth. Pacing pulses are delivered to the cardiac region to enhance one or more effects of the agent in modulating the myocardial tissue growth. In one embodiment, the agent and electrical therapies are delivered by using selected or all the functions provided by system 100, as discussed above. In another embodiment, the agent and electrical therapies are delivered by using selected or all the functions provided by system 300, as discussed above. The embodiments discussed in this document may be combined, other embodiments may be utilized, and/or structural, logical and electrical changes may be made, without departing from the scope of the present invention.

Agents Useful in the Apparatus and Methods of the Invention

In one embodiment, agents within the scope of the present subject matter include, but are not limited to, those which localize stem cells to areas of tissue damage, e.g., myocardial damage, or otherwise modulate tissue growth, e.g., increase vascularization (angiogenesis in the heart), reduce adverse remodeling, modulate fibrosis signaling, enhance stem cell proliferation, enhance cardiomyocyte proliferation, modulate myofibroblast proliferation, or any combination thereof. Those agents including beta-blockers, angiotensin converting enzyme (ACE) inhibitors, and angiotensin receptor blockers, which are delivered by the device of the invention, may be employed alone or in conjunction with other pharmaceutical agents, such as anti-hypertensive agents, anti-arrhythmic agents, pressors, vasopressors, vasodilators, anti-hyperlipidemic agents, anti-anginal agents, ionotropic agents, diuretics, volume expanders, thrombolytics, anti-platelet agents, beta-blockers, ACE inhibitors, and angiotensin receptor blockers, or any combination thereof, which are locally delivered by a device other than a device of the invention or systemically delivered.

In one embodiment, an agent for use in the systems and methods of the invention includes but is not limited to a cytokine, e.g., a cytokine including but not limited to, γIP10, 4-1BBL, 6Ckine, activin, amphiregulan, angiostatin, Apo2L, APRIL, BAFF, ENA-78, eotaxin-1, eotaxin-2, eotaxin-3, EGF, FGF, e.g., bFGF, FGF-8b or FGF-2, FasL, G-CSF, GM-CSF, Gro-α, Gro-β, Gro-γ, HCC-1, HCC-4, HGF, IFNα, IFNβ, IGF-I, IGF-II, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, LARC, MCP-1, MCP-2, MCP-3, MCP-4, MCP-5, MEC, MIF, MIG, MIP1α, MIP1β, NGF, PDGF, RANTES, SCF, SDF-1, TARC, TGF-α, TGF-β, or TPO, or an inhibitor thereof, e.g., ouabain, amlodipine, pentaxifylline, amiodarone, SR33589 or ATI-2001 (Kodama, *Cardiovas. Res.*, 35:13 (1997)), adenosine, VEGF such as VEGF-E (Kibu et al., *BBRC*, 301:371 (2003)), $VEGF_{165}$, or $VEGF_{121}$, NOS, retinoic acid, glycolic acid, angiopoietins, 12-LOX, hydrazones, IGF, cyanomethyl substituted thiazoliums (U.S. Pat. No. 6,610,716), imidazoliums, azolium chroman (U.S. Pat. No. 6,596,745), thiazole (U.S. published application 2002/0022022), imidazole, matrix metallo-proteinases (MMPs) such as MMP-1, 2, 9 or 13, pentafluorosulfanylbenzoyl guanidines (U.S. published application 2003/0216476), AT1 receptor antagonists such as candesartan, inhibitors of MEK or P13-K, PD 098059 or LY294002 (see Hafizi et al., *Cir. Exp. Pharma Physiol.*, 26:511 (1999), ACE inhibitors such as enalapril, cilazapril, enalaprilat, omapatrilat, lisinopril, ramipril, captopril, furosemide, or trandopril, adrenomedullin, pyridoxalbenzoyl hydrozone analogs (U.S. Pat. No. 6,005,009), sulfonamidocarbonyl pyridine-2-carboxamides and pyridine-n-oxides (U.S. Pat. No. 5,610,172), asporin (U.S. published application 2003/30148351), dextran sulfate, pentosan polysulfate, IL-6R inhibitors, leukemia inhibitor factor (LIF), cyclin D2, angiotensin receptor antagonists, e.g., losartan, proangiogenic agents, e.g., those which promote vascularization, such as IGF, EGF, G-CSF, GMCSF, HGF, proliferin, and angiotropin, angiopoietins, e.g., Ang-1, P1GF (placental GF), polysaccharides, HMG-CoA reductase inhibitors, e.g., statins, agents which modulate fibrosis, e.g., TGF-β or inhibitors thereof, e.g., decorin, or TGF-β receptor antagonists, β-adrenergic antagonists, e.g., β-receptor antagonists such as propanolol, metaprolol, carvediol, bunazosin, or isoprenaline, lacidipine, L-type/C-type calcium channel blockers, e.g., mibefradine, L-type calcium channel blockers, e.g., nifedipine, vasodilators, endothelin antagonists, such as endothelin A or B receptor inhibitors, e.g., BQ-123 or BQ788 (Higashi et al., *Br. J. Pharmacol.*, 121:782 (1997)), bosentan, as well as modulators of prolyl-4-hydroxylase (P4H), matrix metalloproteinases, TGF-β, PDGF, EGF, TGF-α, bFGF, IGF, IL-1, TNF-α, e.g., etanercept, tissue inhibitor of metalloproteinase (TIMP), catecholamines, steroids, retinoids, parathyroid hormones, or glucocorticoids, aldosterone, or antagonists thereof, e.g., spironolactone, bradykininase inhibitors, HOE 140 (Villareal et al., *Basic Res. Cardiol.*, 93 Supp 3:4 (1998)), chymase inhibitors, e.g., NK3201 (Sukenaga et al., *Jap. J. Pharmacol.*, 90:218 (2002)), adriamycin, phenyloin, tanshinone VI (Yagi, *J. Pharm. Soc. Japan*, 123:517 (2003), SB203680 (Akiyama-Uchida et al., *Hypertension*, 40:148 (2002), or a calcineurin inhibitor, e.g., FK506.

In particular, to modulate fibrosis, one or more of the following agents may be employed: MEK inhibitors, e.g., PD098059 or LY294002, aldosterone antagonists, chymase inhibitor, e.g., chymostatin or NK3201, tanshinone VI, beta-blockers, such as metoprolol or carvediol, ACE inhibitors, e.g., enalapril, enalaprilat, or cilazapril, calcineurin modulators, e.g., calcineurin inhibitors, beta-blockers, such as metoprolol or carvediol, bradykinin modulators, HGF, modulators of P4H, MMP, TGF-β, PDGF, EGF, TGF-α, bFGF, IGF, IL-1, TNF-α, retinoids, catecholamines, steroids, parathyroid hormone or glucocorticoids; BB-94 (Bigatel et al., *J. Vasc. Surg.*, 29:130 (1999)), pentafluoro sulfanyl benzoyl guanidines, selective AT1 receptor antagonists, phenoxytoin, or modulators of endothelin. In one embodiment, the agent modulates fibroblast proliferation and/or extracellular matrix synthesis or degradation, e.g., by modulating MMPs and TIMP, e.g., TIMP type 1, 2, 3 or 4.

To treat heart failure, one or more of the following agents may be employed: beta-blockers, such as metoprolol or carvediol, ACE inhibitors, e.g., enalapril, enalaprilat, or cilazapril, aldosterone antagonists, endothelin receptor antagonists, TNF-α inhibitors, e.g., etanercept, matrix metalloproteinase inhibitors, vasodilators, β-adrenergic antagonists, angiotensin receptor blockers, e.g., losartan or anomethyl substituted thiaxoliums, imidazoliums, thiaxoles, imidazole, oxazole, pentoxifylline, thalidomide, intravenous immunoglobulin, IL-6, IL-10, IL receptor antagonists, TNF or chemokine modulators.

To treat remodeling, one or more of the following agents may be employed: beta-blockers, such as metoprolol or carvediol, ACE inhibitors, e.g., enalapril, enalaprilat, or cilazapril, aldosterone antagontists, organic nitrites, hydralazine, ramipril, furosemide, a calcium channel blocker, e.g., amlodipine, statins, vasodilators, propranolol, metaprolol, bunazosin, omapatrilat, isoproterenol, endothelin receptor inhibitors, aldosterone antagonists, e.g., spirolactone, AT1 receptor antagonists, bradykinase inhibitors, chymase inhibitors, retinoids, adriamycin, phenoxytoin, adrenomedullin, IL-6R inhibitors, cytokinases, lacidipine, a L-type/C-type calcium channel blocker, e.g., mibefradil, a L-type calcium channel blocker, e.g., nifedipine, or TGF-β inhibitors.

To enhance vasodilation, one or more of the following agents may be employed: EGF, IGF, HGF, proliferin, angiotropin, VEGF, angiopoietin, FGF, SDF-1, PlGF, SCF, IL-8, polysaccharides, HMG-COA reductase inhibitors, NOS, TGF-β, retinoic acid, or a hydrazone (U.S. Pat. No. 6,660,737).

To enhance cardiomyocyte proliferation, one or more of the following agents may be employed: G-CSF, GM-CSF, SDF, IGF, HGF, IL-8, angiotensinogen, or angiotensin type 1 or 2 receptor antagonists.

The present agents may be employed with other agents including but not limited to diuretics such as thiazides, e.g., hydrochlorothizide, loop diuretics, e.g., furosemide, and potassium-sparing agents, e.g., amiloride, spironolactone and triamterene and hydrochlorothiazide, beta-blockers such as bisoprolol, carvedilol, labetolol and metoprolol, angiotensin-converting enzyme inhibitors such as benazepril, captopril, enalapril, fosinopril, lisinopril, perindopril, quinapril, ramipril, trandolapril, delapril, pentopril, moexipril, spirapril, temocapril, and imidapril, calcium channel blockers, alpha blockers, angiotensin II antagonists, e.g., losartan, statins, e.g., atorvastatin, pitavastatin, and pravastatin, or other lipid lowering agents, moxonidine, dihydropyridines, e.g., amlodipine, class III and IV antiarrhythmics, e.g., amiodarone, azimilide, sotalol, dofetilide, and ubutilide, aspirin, selective non-adrenergic imidazoline receptor inhibitors, hebivolol, vasopeptidase inhibitors, e.g., fasidotritat, omapatrilat, samapatrilat, substrates, inhibitors or inducers of cytochrome P450 enzymes, lidocaine, warfarin, oligonucleotides (sense or antisense), natriuretic peptides such as ANP, BNP, NT pro BNP, CNP, and DNP, colforsin daropate hydrochloride (forskilin derivative), antagonists of platelet integrin IIb/IIIa receptors, e.g., abciximab and trofiblant, reteplase, P2 receptor antagonists, e.g., ticlopidine and clopidrogel, mibefradil, hirudin, acetylcholinesterase inhibitors, cardiac glycosides, e.g., digoxin and digitoxin, bradykinin, neutral endopeptidease inhibitors, e.g., neprilysin, direct-acting vasodilators, e.g., hydralazine, nitroglycerin, sodium nitroprusside, catecholamines, dobutramine, dopamine, phosphodiesterase inhibitors, e.g., amrinone and milrinone, TNFα, pentoxifylline, growth hormone, cytokine inhibitors, aldosterone receptor antagonists, calcium sensitizers, nesiritide, 3,5-dicodothyropropionic acid, etomoxir, endothelin receptor antagonists, chlorthiadone, doxazosin, nesiritide, cilostazol, rilmenidine, ticlopidine, dihydropines such as nifedipine and nisoldipine, timolol, propanolol, verapamil, diltiazem, lisinopril, noopept (N-phenylacetyl-L-polyglycine ethylester), cariporide, geldanamycin, radicicol, ibudilast, selective delta (1) agonists such as 2-methyl-4a-alpha-(3-hydroxy-phenyl)-1,2,3,4,4a,5,12,12a-alpha-octahydroquinolinol [2,3,3-g]isoquinoline, monophosphoryl lipid A, RC552, adenosine, adenosine receptor agonists, adenosine triphosphate sensitive channel openers, dipyridamole, fibroblast growth factor, atenolol, ezetimibe, lerosimendan, sirolimus, paclitaxil, actinomycin D, dexamethasone, tacrolimus, everolimus, estradiol, quinapril, tranilast, antiopeptin, trapidil, lacidipine, thiazolidinediones, fenofibrate, lacidipine, nebrivolol, nicotinic acid, probucal, rosuvastatin, gemfibrozil, glitazones, indobugen, alpha-tocopherol, dypiridamole, resins, e.g., cholestyramine and colestipol, bezafibrate, or listat, niacin, heparin, e.g., low molecular weight heparins such as dalteparin sodium and nadroparin calcium, bivalirucin, nitroglycerin, nicorandil, denopamine, eptifibatide, xemilofiban, bofiban, trimetazidine, nicorandil, dalteparin, and isosorbide 5-mononitrate. Additional pharmaceutical agents may be considered based on evidence of their direct or indirect roles in preventing or reducing injury or hemodynamic compromise related to myocardial infarction and/or heart failure. Examples of such pharmaceutical agents include, but are not limited to, L-arginine; nitric oxide (NO); NO derivatives such as nitroxl anion (HNONO—) and peroxynitrite (ONOO—); iNOS, eNOS, and inhibitors such as nitro-L-arginine methyl ester; NO donors such as diethylamine (DEA) NO and nitroglycerin (NTG); and interleukins and interleukin inhibitors.

Sources of Donor Cells for Cell-Based Therapies

Sources for donor cells in cell-based therapies include skeletal muscle derived cells, for instance, skeletal muscle cells and skeletal myoblasts; cardiac derived cells, myocytes, e.g., ventricular myocytes, atrial myocytes, SA nodal myocytes, AV nodal myocytes, and Purkinje cells; bone marrow-derived cells, e.g., mesenchymal cells and stromal cells; smooth muscle cells; fibroblasts; SP cells; or pluripotent cells or totipotent cells, e.g., teratoma cells, hematopoietic stem cells, for instance, cells from cord blood and isolated CD34+ cells, multipotent adult progenitor cells, adult stem cells and embryonic stem cells. In one embodiment, the donor cells are autologous cells, however, non-autologous cells, e.g., xenogeneic cells, may be employed. The donor cells can be expanded in vitro to provide an expanded population of donor cells for administration to a recipient animal. In addition, donor cells may be treated in vitro as exemplified below. Sources of donor cells and methods of culturing those cells are known to the art. See, for example, U.S. Pat. No. 5,130,141 and Jain et al. (*Circulation*, 103, 1920 (2001)), wherein the isolation and expansion of myoblasts from skeletal leg muscle is discussed (see also Suzuki et al., *Circulation*, 104, 1-207 (2001), Douz et al., *Circulation*, III-210 (2000) and Zimmerman et al., *Circulation Res.*, 90, 223 (2002)). Published U.S. Application 20020110910 discusses the isolation of and media for long term survival of cardiomyocytes. U.S. Pat. No. 5,580,779 discusses isolating myocardial cells from human atria and ventricles and inducing the proliferation of those myocardial cells. U.S. Pat. No. 5,103,821 discusses isolating and culturing SA node cells. For SA node cells, the cells may be co-cultured with stem cells or other undifferentiated cells. U.S. Pat. No. 5,543,318 discusses isolating and culturing human atrial myocytes. U.S. Pat. Nos. 6,090,622 and 6,245,566 discusses preparation of embryonic stem cells, while U.S. Pat. No. 5,486,359 discusses preparation of mesenchymal cells.

The donor cells may also be manipulated in vitro to introduce one or more desirable gene products (transgenes) to the cells. Preferably, the transgenic donor cells include a transgene that enhances cellular proliferation, cellular engraftment, cellular survival, cellular differentiation and/or cellular function, e.g., increase angiogenesis or modulate fibrosis, of the donor cells in the recipient. The expression of one or more transgenes may be employed to decrease, replace or supplement (increase) the expression of endogenous genes in the donor cells, e.g., if the donor cells are autologous cells and the donor has an inherited or acquired disease associated with aberrant expression of an endogenous gene in cardiac cells. The expression of one or more transgenes may correct the level of the gene product encoded by the transgene in the donor cells. In one embodiment the expression of the transgene is controlled by a regulatable or tissue-specific, e.g., cardiac myocyte-specific promoter. The transgene may be introduced to donor cells by any means including but not limited to liposomes, electroporation, naked DNA, or viral-mediated transduction, for instance, via adenovirus, adeno-associated virus, retrovirus or lentivirus vectors.

Donor cells may be treated in vitro by subjecting them to mechanical, electrical, or biological conditioning, or any combination thereof. The conditioning may include continuous or intermittent exposure to the exogenous stimuli. Preferred exogenous agents include those which enhance the survival, engraftment, differentiation, proliferation and/or function of donor cells after transplant.

A. Mechanical Conditioning

Mechanical conditioning includes subjecting donor cells to a mechanical stress that simulates the mechanical forces applied upon cardiac muscle cells in the myocardium due to the cyclical changes in heart volume and blood pressure. In one embodiment, a cyclic mechanical stress is applied to the donor cells. In one embodiment, the cyclical mechanical stress applied to donor cells results in the cyclical deformation of these cells, resembling the cyclical deformation (contraction) of cardiac muscle cells in vivo. The mechanical stress includes subjecting one or more donor cells, preferably a population of donor cells, to a mechanical force in one dimension and in one direction, or alternatively, in one dimension and in two or more opposite directions, for example, causing the donor cells to stretch and relax at a predetermined frequency for a predetermined duration. Mechanical conditioning can result in donor cells that are capable of contracting upon excitation by action potentials.

Mechanical conditioning preferably alters gene expression, protein synthesis, and/or the activity of one or more cellular kinases in donor cells, and in one embodiment results in proliferation and/or differentiation of the donor cells. In one embodiment, mechanical conditioning of donor cells results in an altered expression profile, e.g., an altered expression profile for genes encoding BMP, VEGF, angiotensin II, and the like, in the donor cells. In one embodiment, mechanical conditioning of donor cells results in an increase in the number and/or activity of contractile elements including actin and myosin filaments, which are protein structures that interact with each other during muscle contraction. Donor cells subjected to mechanical conditioning thus develop contractility that is characteristic of muscle cells.

In one embodiment, the mechanical conditioning includes subjecting donor cells to a mechanical force so that the donor cells are physically extended in at least one direction by approximately 5% to 20% of their length, and at a frequency of 0.25 to 2 Hz. In other words, at least one donor cell is forced to increase its length by 5% to 20% at 0.25 to 2 times per second. This simulates the mechanical tension which cardiac muscle cells are subject to under physiological conditions in vivo. In one embodiment, donor cells are plated on a controllably deformable culturing substrate in the presence of culturing media. The substrate is cyclically deformed to simulate the mechanical displacement of cardiac muscle. In one specific embodiment, the substrate includes a distensible strip made of medical grade silicone. Donor cells are plated on the distensible strip. The distensible strip is stretched and released, such that the donor cells on it change their length with the distensible strip in a manner simulating the cardiac muscle cells in vivo. One example of such an apparatus for applying mechanical stress to cells in a culture is given in Terracio et al., *In Vitro Cellular & Developmental Biology*, 24(1), 53-58, 1988, where the silicone strip is subject to calibrated mechanical tension created with a variable speed motor.

In one embodiment, the mechanical conditioning is applied continuously for a predetermined period of time. In one specific embodiment, the predetermined period is in the range of 1 to 14 days. In another embodiment, the mechanical conditioning is applied intermittently for a predetermined period of time interrupted by one or more resting (non-stimulating) periods. In one specific embodiment, the mechanical conditioning is applied with a duty cycle that is in the range of 5% to 75% for a predetermined period that is in the range of 1 to 14 days.

B. Electrical Conditioning

Electrical conditioning includes subjecting donor cells to electrical conditions that simulate the electrical conditions in the myocardium which result in contraction of the heart. In the heart, contraction results primarily from the contractions of atrial and ventricular muscle fibers. Contraction of atrial and ventricular muscle fibers is slower and is of a longer duration than the contraction of skeletal muscle. Cardiac muscle and skeletal muscle, however, share a number of common anatomic characteristics. In the same manner as skeletal muscle, cardiac muscle is made up of elongated fibers with transverse dark and light bands. The dark bands correspond to the boundaries between cells. Each fiber is made up of individual cells connected in series with each other. Cardiac muscle includes myofibrils, which are the longitudinal parallel contractile elements composed of actin and myosin filaments that are almost identical to those of the skeletal muscle. The actin and myosin filaments interdigitate and slide along each other during contraction. Contraction is caused by action potentials that propagate along or spread over the muscle fibers. The propagation of action potentials results from changes in the electrical potential across muscle cell membranes, referred to as membrane potential. The changes in the membrane potential are in turn caused by flow of sodium, potassium, and/or calcium ions across the muscle cell membranes through ion channels, which are formed by protein molecules in the cell membranes. Some types of muscle include protein structures called gap junctions through which ions flow from one muscle cell to another. Gap junctions allow the flow of ions, and hence the propagation of action potentials, directly from one cell to another. Cardiac muscle has at least two unique anatomic characteristics: a high density of calcium-sodium channels and a high density of gap junctions. These characteristics distinguish cardiac muscle from skeletal and other types of muscle.

Action potential propagates in skeletal muscle mainly via the sudden opening of fast sodium channels that allow sodium ions to enter the muscle cells. Each opening of a fast sodium channel lasts for only a few ten-thousandths of a second. In contrast, cardiac muscle includes both fast sodium channels and slow calcium-sodium channels that allow both calcium and sodium to enter the muscle cells. Each opening of a slow calcium-sodium channel lasts for several tenths of a second. This results in the long duration of contraction, which characterizes cardiac muscle.

Gap junctions in cardiac muscle fibers allow relatively free flow of ions across the cell membranes along the fiber axes. Thus, action potentials travel from one cell to another with little resistance. Cardiac muscle is a syncytium (mass of fused cells) with muscle fibers arranged in a latticework in which the fibers branch, merge, and branch again. When one cell in the syncytium becomes excited, the action potential propagates from cell to cell and spreads throughout the latticework interconnections. The heart includes two syncytiums, the atrial syncytium and the ventricular syncytium. In a normal heart, action potentials are conducted from the atrial syncytium to the ventricular syncytium through a conduction system, the A-V bundle, and the atrial syncytium contracts before the ventricular syncytium.

In one embodiment, electrical conditioning includes providing electrical stimuli such as cardiac pacing pulses to the donor cells in culture so as to cause them to contract. In another embodiment, the electrical conditioning includes providing a static electrical field to the donor cells in culture. Electrical conditioning can result in the donor cells proliferating and differentiating into cardiac muscle cells, and preferably results in cells functioning as cardiac muscle cells.

In one embodiment, electrical conditioning of donor cells results in cells with one or more characteristics of cardiac muscle cells, including a high density of calcium-sodium channels and a high density of gap junctions. Such electrical conditioning may occur in vitro and/or in vivo. Moreover, once the donor cells are implanted in the myocardium, they are subject to the pattern of contractions in the myocardium and may, if they are not cardiac muscle cells, differentiate into cardiac muscle cells. In one embodiment, the donor cells are electrically conditioned prior to implantation into the myocardium. In one embodiment, the electrical conditioning includes subjecting the donor cells to an artificially induced contraction pattern that simulates the physiological contractions of cardiac muscle cells in vivo. The contraction pattern is induced by electrical stimulation such as by cardiac pacing. In a further embodiment, the donor cells are also subjected to an electrical field stimulation that simulates the environment in the myocardium. Electrical conditioning of donor cells, including cardiac pacing and/or field stimulation, may result in an altered expression profile of the donor cells, including increased calcium-sodium channel expression and/or increased expression and/or formation of gap junctions. For instance, electrical conditioning may increase angiotensin II or VEGF expression, which in turn increases gap junction formation.

In one embodiment, pacing pulses are generated by a pacemaker or any pulse generator capable of producing the pacing pulses. The donor cells are placed in a culturing media including fluids which simulate the extracellular fluid of the myocardium. The pacing pulses are delivered to the donor cells through two electrodes placed in the culture. Parameters controlling the delivery of the cardiac pacing pulses include pacing rate, pacing voltage, and pacing pulse width, which are each selected from a physiological range to simulate the electrical activities within the myocardium. In one specific embodiment, the pacing rate is in the range of 15 to 120 beats per minute; the pacing voltage is in the range of 0.1 to 10 volts; and the pacing pulse width is in the range of 0.1 to 10 milliseconds. In one embodiment, cardiac pacing is applied to the donor cells continuously for a predetermined period of time. In one specific embodiment, the predetermined period of time is in the range of 1 to 14 days. In another embodiment, cardiac pacing is applied intermittently to the donor cells for a predetermined period that is interrupted by one or more resting (non-pacing) periods. In one specific embodiment, cardiac pacing is applied to the donor cells with a duty cycle in the range of 5% to 75% for a predetermined period that is in the range of 1 to 14 days.

In one embodiment, a static electrical field is applied to a donor cell culture. In one specific embodiment, the field strength is in the range of 1 to 100 volts per meter. In one embodiment, the electrical field is applied continuously for a predetermined period. In one specific embodiment, the predetermined period is in the range of 1 to 14 days. In another embodiment, the electrical field is applied for a predetermined period that is interrupted by one or more resting (non-stimulation) periods. In one specific embodiment, the electrical field is applied with a duty cycle of 5% to 75% for a predetermined period that is in the range of 1 to 14 days.

C. Biological Conditioning

Biological conditioning includes subjecting donor cells to exogenous agents, e.g., differentiation factors, growth factors, angiogenic proteins, survival factors, and cytokines, as well as to expression cassettes (transgenes) encoding a gene product including, but not limited to, an angiogenic protein, a growth factor, a differentiation factor, a survival factor, a cytokine, a cardiac cell-specific structural gene product, a cardiac cell-specific transcription factor, or a membrane protein, e.g., a gap junction protein, or comprising an antisense sequence, for instance, a ribozyme, or any combination thereof. The expression cassette optionally includes at least one control element such as a promoter, optionally a regulatable promoter, e.g., one which is inducible or repressible, an enhancer, or a transcription termination sequence. Preferably, the promoter and/or enhancer is one which is cell- or tissue-specific, e.g., cardiac cell-specific. For instance, the enhancer may be a muscle creatine kinase (mck) enhancer, and the promoter may be an alpha-myosin heavy chain (MyHC) or beta-MyHC promoter (see Palermo et al., *Circ. Res.* 78, 504 (1996)).

Transgenes

In one embodiment, the transgene encodes a gene product including but not limited to an angiogenic protein, e.g., a fibroblast growth factor (FGF) such as acidic-FGF, basic-FGF, FGF-3, FGF-4, FGF-5, FGF-6, FGF-7, FGF-8 and FGF-9, vascular endothelial growth factor (VEGF), e.g., VEGF-A, VEGF-B, VEG-C, VEGF-D, VEGF-E, VEGF-F, $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., TGF-beta$_1$, leukemia inhibitory factor (LIF) alone or in combination with other cytokines, a myogenic factor, e.g., myoD, RyRZ (cardiac ryanodine receptor), Del I, myogenin, parvalbumin, Myf5, and MRF, transcription factors (GATA such as GATA-4 and dHAND/eHAND), cytokines such as cardiotrophin-1, calsequestrin, neuregulin, for instance, neuregulin 1, 2 or 3, and homeobox gene products, e.g., Csx, tinman, and the NKx family, e.g., NKx 2.5, transferrin, platelet-derived growth factor (PDGF), epidermal growth factor (EGF), adrenocorticotrophin, macrophage colony-stimulating factor, protein kinase C activators, endothelial growth factor, mutant G protein receptor kinase (GRK), adenylyl cylase (AC), e.g., cardiac AC such as human type II, V or VI adenyl cylase (U.S. Pat. No. 6,436,672), V2 vasopressin receptor, sarcoplasmic reticulum $Ca^{2+}$ ATPase (SERCA2a), phospholambam, N-cadherin, connexin-40, connexin-41, connexin-42, connexin-43, or connexin-45, contractable proteins, e.g., myosin heavy chain (MyHC), myosin light chain (MyLC), myosin binding protein C, actin, tropomyosin, troponin, e.g., troponin T, M protein, tropomodulin, myofibrillar protein, stress related protein, e.g., heat shock protein (HSP) such as HSP70i, HSP27, HSP40 or HSP60, $\alpha$-1 antitrypsin, HF1-a, HF-1b, MEF2, BMP-2, BMP-4, BMP-17, BMP-18, Pax7, oxytocin, oxytocin receptor, myocyte nuclear factor, Frzb (see published U.S. application 20020147329), Rb-interacting zinc finger protein (U.S. Pat. No. 6,468,985), eNOS, iNOS, serine/threonine protein phosphatase, cardiac hypertrophy factor, CT-1, $\alpha$, $\beta$, $\gamma$ or $\delta$ sarcoglycan, hypoxia inducible factor 1$\alpha$, bcl-2, FasL, cytokine gp 130 receptor, gp130, Akt, adenosine A3 receptor, angiogenin, e.g., angiogenin-1 or angiogenin-2, TNF$\alpha$, dystrophin, tafazzin, desmin, lamin, troponin C, caspase inhibitors, ERK-type of MAP kinases (p42 and p44, anti-apoptosis), IL-1B, serum releasing factor, and ILGF (I and II), NGF, growth hormone, e.g., human growth hormone, angiotensin, e.g., angiotensin II, hepatocyte growth factor (HGF), ARK$_{Ct}$, endothelial GF121, angiotensin type II receptor, p16INK4a, sodium channel protein, e.g., SCN5A, C reactive protein, MiRPI, cardiac endothelin-1, KCNEI (I$_{Ks}$), protein kinase C, HIF-1$\alpha$, p38MAPK, Cox-2, phospholamban, matrix metalloproteinases, adrenergic receptors (AR) and kinases therefore, e.g., betaAR and betaARK, cytochrome oxidase B subunit III, ATP synthase subunit 6, calcium channel proteins such as voltage gated Ca2+ channels, potassium channel proteins such as KCNA5 (Kv1.5), KCND2(Kv4.2), KCND3 (Kv 4.3, I$_{to}$), KCNEI (minK), KCNE2, KCNQ1, as well as K+ inwardly rectifying channels such as Kir3.1 (KCNJ3), KCNH2 (HERG, I$_{kr}$), Kv4.3, Kir3.4, Kir6.1 and Kir6.2, the sodium-calcium exchanger (I$_{Na/Ca}$), e.g., NCKX1-4, HCN, Kir 2.1, Kir3.1/ 3.4, ERG, KvLQT1, Kv4.2/4.3, Kv1.4, KChlP2, Kv1.5/3.1, Ca$_v$1.2, Ca$_v$1.3, Ca$_v$3.1, Ca$_v$3,3, Na$_v$1.5, platelet-derived endothelial-cell growth factor (PD-ECGF), transforming growth factor-$\alpha$ (TGF-$\alpha$), transforming growth factor-$\beta$ (TGF-$\beta$), thrombospondin (TSP), proliferin, ephrin-A1 (B61), e-selectin, chicken chemotactic and angiogenic factor (cCAF), leptin, heparin affin regulatory peptide (HARP), platelet derived growth factor (PDGF), e.g., PDGF-AA, PDGF-AB or PDGF-BB, or heparin.

In another embodiment, e.g., for cells from a mammal with an inherited or acquired disorder such as one characterized by overexpression of certain endogenous genes, the transgene may comprise antisense or ribozyme sequences which substantially correspond to the reverse complement of at least a portion of the endogenous gene, and which, when expressed in a host cell, results in a decrease in the expression of the endogenous gene. Alternatively, the transgene may comprise sequences which, after homologous recombination with the endogenous gene, result in a decrease in the expression of the endogenous gene. For instance, the use of antisense vectors resulting in the decreased expression of the following gene products may be beneficial in autologous cell therapy, gene products including, but not limited to, those which induce apoptosis, e.g., Fas, Bax1 and ApoI, or a Na/Ca exchanger, or a mitogen-activated protein (MAP) kinase, Janus kinase (JAK)/signal transducer or activator of transcription, calcium/calmodulin-dependent protein phosphatase, calcineurin, carnitine palmoyl-transferase I, matrix metalloproteinase, eNOS, iNOS, serine/threonine protein phosphatase, or stress response mitogen activated protein kinase, e.g., Junk and p38MAPK.

For purposes of the present invention, control elements, such as muscle-specific and inducible promoters, enhancers and the like, will be of particular use. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell Biol.,* 11, 4854 (1991)); control elements derived from the human skeletal actin gene (Muscat et al., *Mol. Cell Bio.,* 7; 4089 (1987)) and the cardiac actin gene; muscle creatine kinase sequence elements (Johnson et al., *Mol. Cell Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors (Semenza et al., *Proc. Natl. Acad. Sci. USA,* 88, 5680 (1991); Semenza et al., *J. Biol. Chem.,* 269, 23757); steroid-inducible elements and promoters, such as the glucocorticoid response element (GRE) (Mader and White, *Proc. Natl. Acad. Sci. USA,* 90, 5603 (1993)); the fusion consensus element for RU486 induction; and elements that provide for tetracycline regulated gene expression (Dhawan et al., *Somat. Cell. Mol. Genet.,* 21, 233 (1995); Shockett et al., *Proc. Natl. Acad. Sci. USA,* 92, 6522 (1995)).

Cardiac cell restricted promoters include but are not limited to promoters from the following genes: a $\alpha$-myosin heavy chain gene, e.g., a ventricular $\alpha$-myosin heavy chain gene, $\beta$-myosin heavy chain gene, e.g., a ventricular $\beta$-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac $\alpha$-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal $\alpha$-actin gene, as well as an artificial cardiac cell-specific promoter.

Further, chamber-specific promoter promoters may also be employed, e.g., for atrial-specific expression, the quail slow myosin chain type 3 (MyHC3) or ANP promoter, may be employed. For ventricle-specific expression, the iroquois homeobox gene may be employed. Nevertheless, other promoters and/or enhancers which are not specific for cardiac cells or muscle cells, e.g., RSV promoter, may be employed in the expression cassettes and methods of the invention.

Other sources for promoters and/or enhancers are promoters and enhancers from the Csx/NKX 2.5 gene, titin gene, $\alpha$-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

Preferably, the transgenic donor cells include a transgene that enhances the proliferation, engraftment, survival, differentiation and/or function of the donor cells and/or decreases, replaces or supplements (increases) the expression of endogenous genes in the donor cells. In one embodiment, the expression of the transgene is controlled by a regulatable or tissue-specific, e.g., cardiomyocyte-specific promoter. Optionally, a combination of vectors each with a different transgene can be employed.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology,* 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Preferred recombinant viruses to deliver exogenous transgenes to cells include recombinant lentiviruses, retroviruses, adenoviruses, adeno-associated viruses (AAV), and herpes viruses including cytomegalovirus.

In one embodiment, recombinant AAV (rAAV) is employed to deliver a transgene to donor cells. Myoblasts are transduced either while actively dividing, or as a differentiated cell culture. Differentiation is induced by placing subconfluent myoblasts in DMEM containing 2% horse serum and standard concentrations of glutamine and penicillin-streptomycin for an interval of four days prior to transduction. Verification of differentiation is by microscopic analysis to determine the presence of multinucleated myotubes in culture. Myotubes (differentiated cells) or myoblasts (dividing cells) are transduced in culture.

Other Exogenous Agents

In another embodiment, the exogenous agent includes but is not limited to an angiogenic protein, e.g., a FGF such as acidic-FGF, basic-FGF, and FGF-5, VEGF, e.g., $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., $TGF\text{-}beta_1$, LIF alone or in combination with other cytokines, a myogenic factor, e.g., myoD, RyRZ (cardiac ryanodine receptor), Del I, myogenin, parvalbumin, Myf5, and MRF, GATA such as GATA-4 and dHAND/eHAND, cytokines such as cardiotrophin-1, calsequestrin, neuregulin, for instance, neuregulin 1, 2 or 3, and homeobox gene products, e.g., Csx, tinman, and the NKx family, e.g., NKx 2.5, transferrin, PDGF, EGF, adrenocorticotrophin, macrophage colony-stimulating factor, protein kinase C activators, endothelial growth factor, β2 adrenergic receptor (1 or 2), mutant G protein receptor kinase (GRK), AC, e.g., cardiac AC such as human type II, V or VI adenyl cylase (U.S. Pat. No. 6,436,672), V2 vasopressin receptor, SERCA2a, phospholambam, β-adrenergic receptor kinase, N-cadherin, connexin-40, connexin-42, connexin-43, MyHC, MyLC, myosin binding protein C, actin, tropomyosin, troponin, e.g., troponin T, M protein, tropomodulin, myofibrillar protein, stress related protein, e.g., HSP such as HSP70i, HSP27, HSP40 or HSP60, α-1 antitrypsin, HF1-a, HF-1b, MEF2, HGF, BMP-2, BMP4, BMP-17, BMP-18, Pax7, oxytocin, oxytocin receptor, myocyte nuclear factor, Frzb (see published U.S. application 20020147329), Rb-interacting zinc finger protein (U.S. Pat. No. 6,468,985), eNOS, iNOS, serine/threonine protein phosphatase, cardiac hypertrophy factor, CT-1, α, β, γ or δ sarcoglycan, hypoxia inducible factor 1α, bcl-2, FasL, cytokine gp 130 receptor, gp130, Akt, adenosine A3 receptor, angiogenin, e.g., angiogenin-1 or angiogenin-2, TNFα, dystrophin, tafazzin, desmin, lamin, troponin C, caspase inhibitors, ERK-type of MAP kinases (p42 and p44, anti-apoptosis), IL-1B, serum releasing factor, and ILGF (I and II), NGF, growth hormone, e.g., human growth hormone, angiotensin, e.g., angiotensin II, inotropes, norepinephrine, retinoic acid, preconditioned media, e.g., from ES cells which contains a plurality of growth factors, or other biological agents disclosed herein, or dexamethasone or 5 azacytidine. Such agents may also be administered to a mammal prior to, during, or after cell therapy, or any combination thereof.

Compositions Dosages and Routes of Administration

The amount of agent administered, including agents released from a device of the invention or agents including cells and/or gene therapy vectors which are exogenously administered in conjunction with electrical and agent therapies described herein, will vary depending on various factors including, but not limited to, the agent chosen, the disease, whether prevention or treatment is to be achieved, and if the agent is modified for bioavailability and in vivo stability. Thus, the agents of the invention may be employed in conjunction with other therapies, e.g., therapies for ischemia or arrhythmias, including gene therapies and/or cell therapies, e.g., see U.S. patent application Ser. No. 10/723,258, filed on Nov. 25, 2003, entitled "METHOD AND APPARATUS FOR CELL AND ELECTRICAL THERAPY OF LIVING CELLS" and U.S. patent application Ser. No. 10/788,906, filed on Feb. 27, 2004, entitled "METHOD AND APPARATUS FOR DEVICE CONTROLLED GENE EXPRESSION", the disclosures of which are incorporated herein by reference in their entirety.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes, although local administration of at least one agent via an implantable device is a preferred embodiment of the invention. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

Pharmaceutical formulations containing the agents of the invention can be prepared by procedures known in the art using well known and readily available ingredients. For example, the agent can be formulated with common excipients, diluents, or carriers. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The formulations can include buffering agents such as calcium carbonate, magnesium oxide and magnesium carbonate, as well as, inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and gelatin, microcrystalline cellulose, sodium lauryl sulfate, starch, talc, or titanium dioxide, or liquid vehicles such as polyethylene glycols (PEGs) and vegetable oil.

The pharmaceutical formulations of the agents of the invention can also take the form of an aqueous or anhydrous solution or dispersion, or alternatively the form of an emulsion or suspension.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

Additionally, the agents are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, epicardial patch, leads, and the like.

The formulations and compositions described herein may also contain other ingredients such as antimicrobial agents, or preservatives. Furthermore, as described herein the active ingredients may also be used in combination with other therapeutic agents, or therapies, for instance, cell therapy.

The cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered to, e.g., injected, the region of interest, for instance, infarcted and tissue surrounding infarcted tissue. Agents which may enhance cardiac function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like. Such agents may optionally be present in a composition comprising the donor cells or administered separately.

The cells are administered during a prophylactic, diagnostic or therapeutic vascular procedure or an invasive or minimally invasive surgical procedure. In one embodiment, the cells are administered post-MI, within hours, e.g., 1 to 12 hours, to days, e.g., 1 to 2 days, and up to one or more weeks after MI. Preferably, the administration of donor cells is prior to scar formation. The cells may be administered intravenously, transvenously, intramyocardially or by any other convenient route, and delivered by a needle, catheter, e.g., a catheter which includes an injection needle or infusion port, or other suitable device.

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A system configured to treat a heart having a myocardial infarct region, the system comprising:
   one or more agents modulating myocardial tissue growth;
   an implantable agent delivery device containing the one or more agents and adapted to release the one or more agents to a cardiac region including at least portions of the myocardial infarct region; and
   an implantable cardiac rhythm management (CRM) device including:
      a pacing circuit to deliver pacing pulses to the cardiac region;
      a pacing controller adapted to control the delivery of the pacing pulses to enhance the modulation of myocardial tissue growth by the one or more agents, wherein the pacing controller comprises a pacing algorithm execution module programmed to execute a remodeling control therapy (RCT) pacing algorithm;
      a remodeling sensor adapted to sense a signal indicative of a size of the myocardial infarct region; and
      an agent delivery controller adapted to produce an agent delivery control signal using the sensed signal indicative of the size of the myocardial infarct region, wherein the implantable agent delivery device is adapted to release the one or more agents according to the agent delivery control signal.

2. The system of claim 1 wherein the implantable agent delivery device includes an agent reservoir containing the one or more agents and an reservoir agent level detector.

3. The system of claim 1, wherein the implantable agent delivery device is incorporated into an additional implantable device other than the implantable CRM device.

4. The system of claim 1, wherein the one or more agents alter one or more mechanical properties of tissue in the cardiac region.

5. The system of claim 1, wherein the one or more agents alter stress, work or strain in the cardiac region.

6. The system of claim 1, wherein the one or more agents promote vascularization in the cardiac region.

7. The system of claim 1, wherein the one or more agents reduce adverse remodeling of tissue in the cardiac region.

8. The system of claim 1, wherein the one or more agents modulate hypertrophic signaling in the cardiac region.

9. The system of claim 8, wherein one agent is an endothelin receptor blocker.

10. The system of claim 1, wherein the one or more agents modulate fibrosis signaling in the cardiac region.

11. The system of claim 1, wherein the one or more agents enhance localization, implantation, or proliferation of stem cells at the cardiac region.

12. The system of claim 11, wherein the one or more agents include one or more of stem cell growth factor (SCF), granulocyte colony-stimulation factor (G-CSF), granulocyte macrophage colony-stimulating growth factor (GM-CSF), stem cell homing factor (SDF-1), bone morphogenetic protein 2 (BMP-2), or Wnt protein, or a gene encoding SCF, G-CSF, GM-CSF, SDF-1, BMP-2 or a Wnt protein.

13. The system of claim 1, wherein at least one agent is a cytokine.

14. The system of claim 1, wherein at least one agent is hepatocyte growth factor (HGF), insulin-like growth factor (IGF), fibroblast growth factor (FGF), or transforming growth factor-beta (TGF-β), or a gene encoding HGF, IGF, FGF, or TGF-β.

15. The system of claim 1, wherein the pacing controller comprises a pacing algorithm execution module programmed to execute a cardiac resynchronization therapy (CRT) pacing algorithm.

16. The system of claim 1, further comprising a pacing lead connected to the implantable CRM device, the pacing lead including at least one electrode to be disposed in or near the myocardial infarct region.

17. The system of claim 16, wherein the pacing lead is an agent eluting pacing lead including the implantable agent delivery device near the at least one electrode.

18. The system of claim 1, wherein the implantable agent delivery device is configured to be incorporated into a stent to be disposed in or near the myocardial infarct region.

19. The system of claim 1, wherein the implantable agent delivery device comprises an agent eluting epicardial patch to be disposed in or near the myocardial infarct region.

20. The system of claim 1, wherein the implantable CRM device further comprises a sensor to sense a signal indicative of a need for the release of the one or more agents.

21. The system of claim 20, wherein the sensor comprises an ischemia sensor to sense a signal indicative of an ischemic condition.

22. The system of claim 20, wherein the sensor comprises an cardiac sensing circuit to sense at least one electrogram indicative of arrhythmia.

23. The system of claim 20, wherein the sensor comprises a displacement sensor to sense a signal indicative of a strain of myocardial tissue.

24. The system of claim 20, wherein the sensor comprises a sensor to sense hypertrophic signaling.

25. The system of claim 24, wherein the sensor comprises a sensor to sense the concentration of endothelin-1, brain natriuretic peptide (BNP) or p38MAPK.

26. The system of claim 20, wherein the sensor comprises a metabolic sensor to sense a signal indicative of a metabolic need of a body.

27. The system of claim 20, wherein the sensor comprises a temperature sensor to sense a signal indicative of a perfusion of thermal energy through myocardial tissue.

28. The system of claim 20, wherein the sensor comprises a metabolic sensor to sense one or more signals indicative of a cardiac metabolism level.

29. The system if claim 28, wherein the metabolic sensor includes at least one of a pH sensor, an oxygen pressure ($PO_2$) sensor, a carbon dioxide pressure ($PCO_2$) sensor, a glucose sensor, a creatine sensor, a C-creative protein sensor, a creatine kinase sensor, and a creatine kinase-MB sensor.

30. The system of claim 1, wherein the implantable agent delivery device comprises an electrically controlled polymer containing the one or more agents, and wherein the polymer is adapted to release the one or more agents at a rate controlled by an amplitude of the agent delivery control signal.

31. The system of claim 1, wherein the agent delivery controller comprises a command receiver to receive an external command, and wherein the agent delivery controller is adapted to produce the agent delivery control signal in response to the external command.

32. The system of claim 31, further comprising an external system communicatively coupled to the implantable CRM device, the external system including a command transmitter to transmit the external command to the implantable CRM device.

33. The system of claim 32, wherein the external system comprises a user input to receive a user command, and wherein the command transmitter is adapted to transmit the external command in response to the user command.

34. The system of claim 33, wherein the external system comprises a programmer.

35. The system of claim 33, wherein the external system comprises:
an external device communicatively coupled to the implantable CRM device;
a network coupled to the external device; and
a remote device coupled to the network to provide for communication with the implantable CRM device from a remote location.

36. The system of claim 35, wherein the external device comprises the user input.

37. The system of claim 35, wherein the remote device comprises the user input.

38. The system of claim 1, wherein the implantable agent delivery device is communicatively coupled to the implantable CRM device via telemetry.

39. The system of claim 1, further comprising one or more pacing leads, coupled to the implantable CRM device, for delivering the pacing pulses to the cardiac region, and wherein the remodeling sensor comprises two or more piezoelectric crystals incorporated into the one or more pacing leads.

40. The system of claim 1, wherein the remodeling sensor comprises a hypertrophic sensor adapted to sense a signal indicative of a degree of myocardial hypertrophy.

41. The system of claim 1, wherein the remodeling sensor comprises a chemical sensor adapted to sense a concentration of endothelin-1, brain natriuretic peptide (BNP) or p38MAPK.

* * * * *

UNITED STATES PATENT AND TRADEMARK OFFICE
CERTIFICATE OF CORRECTION

PATENT NO. : 7,764,995 B2
APPLICATION NO. : 10/862716
DATED : July 27, 2010
INVENTOR(S) : Steven D. Girouard et al.

It is certified that error appears in the above-identified patent and that said Letters Patent is hereby corrected as shown below:

In column 32, line 38, in Claim 2, delete "an" and insert -- a --, therefor.

In column 32, line 39, in Claim 3, delete "claim 1," and insert -- claim 2, --, therefor.

In column 32, line 62, in Claim 12, delete "stern" and insert -- stem --, therefor.

In column 33, line 32, in Claim 22, delete "an" and insert -- a --, therefor.

In column 33, line 51, in Claim 29, delete "if" and insert -- of --, therefor.

Signed and Sealed this

Thirtieth Day of November, 2010

David J. Kappos
*Director of the United States Patent and Trademark Office*